(12) United States Patent
Albadawi et al.

(10) Patent No.: US 10,467,509 B2
(45) Date of Patent: Nov. 5, 2019

(54) COMPUTATIONALLY-EFFICIENT HUMAN-IDENTIFYING SMART ASSISTANT COMPUTER

(71) Applicant: Microsoft Technology Licensing, LLC, Redmond, WA (US)

(72) Inventors: Haithem Albadawi, Redmond, WA (US); Zongyi Liu, Issaquah, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 0 days.

(21) Appl. No.: 15/636,422

(22) Filed: Jun. 28, 2017

(65) Prior Publication Data

US 2018/0232902 A1 Aug. 16, 2018

Related U.S. Application Data

(60) Provisional application No. 62/459,020, filed on Feb. 14, 2017, provisional application No. 62/482,165, filed on Apr. 5, 2017.

(51) Int. Cl.
*G06K 9/00* (2006.01)
*G06K 9/72* (2006.01)
(Continued)

(52) U.S. Cl.
CPC ............. *G06K 9/726* (2013.01); *A61B 5/0205* (2013.01); *A61B 5/0507* (2013.01); *A61B 5/117* (2013.01);
(Continued)

(58) Field of Classification Search
CPC ................ G06K 9/726; G06K 9/00124; G06K 9/00255; G06K 9/00261; G06K 9/00288;
(Continued)

(56) References Cited

U.S. PATENT DOCUMENTS 6,067,673 A 5/2000 Paese et al.
6,119,088 A 9/2000 Ciluffo
(Continued)

FOREIGN PATENT DOCUMENTS

EP 2947476 A1 11/2015
GB 2522922 A 8/2015
(Continued)

OTHER PUBLICATIONS

"Train the Natural Language Processing Classifiers", Retrieved From <<https://www.mindmeld.com/docs/train_the_natural_language_processing_classifiers.html>>, Retrieved on: May 2, 2017, 10 Pages.
(Continued)

*Primary Examiner* — Ping Y Hsieh
(74) *Attorney, Agent, or Firm* — Alleman Hall Creasman & Tuttle LLP

(57) ABSTRACT

A computationally-efficient method for a smart assistant computer to track a human includes receiving data from one or more sensors configured to monitor a physical environment. The data is computer-analyzed to recognize presence of a human in the physical environment, and upon confirming an identity of the human, a first level of computational resources of the smart assistant computer is dedicated to track the human. Upon failing to confirm the identity of the human while a known user is present, a second level of computational resources of the smart assistant computer, greater than the first level, is dedicated to determine the identity of the human. Upon failing to confirm the identity of the human while the known user is absent, a third level of computational resources of the smart assistant computer, is dedicated to determine the identity of the human.

20 Claims, 10 Drawing Sheets

(51) Int. Cl.

| | |
|---|---|
| *G06T 7/70* | (2017.01) |
| *G06K 9/62* | (2006.01) |
| *G06F 3/16* | (2006.01) |
| *G10L 15/18* | (2013.01) |
| *G06N 20/00* | (2019.01) |
| *G06T 7/73* | (2017.01) |
| *G06T 7/246* | (2017.01) |
| *G01S 5/18* | (2006.01) |
| *G06T 7/60* | (2017.01) |
| *G10L 15/22* | (2006.01) |
| *G10L 15/28* | (2013.01) |
| *H04R 1/40* | (2006.01) |
| *H04R 3/00* | (2006.01) |
| *H04N 5/33* | (2006.01) |
| *H04N 7/18* | (2006.01) |
| *G10L 15/02* | (2006.01) |
| *G06N 5/02* | (2006.01) |
| *G06N 5/04* | (2006.01) |
| *G10L 15/06* | (2013.01) |
| *G10L 15/24* | (2013.01) |
| *G06F 17/27* | (2006.01) |
| *G10L 15/26* | (2006.01) |
| *G10L 15/19* | (2013.01) |
| *G10L 15/08* | (2006.01) |
| *G10L 15/32* | (2013.01) |
| *G10L 25/51* | (2013.01) |
| *H04L 29/06* | (2006.01) |
| *A61B 5/0205* | (2006.01) |
| *A61B 5/05* | (2006.01) |
| *G01S 13/72* | (2006.01) |
| *G06F 21/35* | (2013.01) |
| *G07C 9/00* | (2006.01) |
| *G08B 13/14* | (2006.01) |
| *G06F 3/01* | (2006.01) |
| *G06F 3/0482* | (2013.01) |
| *G06F 3/0484* | (2013.01) |
| *H04N 21/231* | (2011.01) |
| *G01S 5/28* | (2006.01) |
| *G06F 1/3206* | (2019.01) |
| *G06F 1/3231* | (2019.01) |
| *G06F 1/324* | (2019.01) |
| *G06F 3/03* | (2006.01) |
| *G06F 21/32* | (2013.01) |
| *H04L 12/58* | (2006.01) |
| *G10L 17/04* | (2013.01) |
| *G10L 17/08* | (2013.01) |
| *G06T 7/292* | (2017.01) |
| *H04L 29/08* | (2006.01) |
| *H04N 21/422* | (2011.01) |
| *H04N 21/442* | (2011.01) |
| *H04N 5/232* | (2006.01) |
| *H04W 4/029* | (2018.01) |
| *H04W 4/33* | (2018.01) |
| *A61B 5/00* | (2006.01) |
| *A61B 5/11* | (2006.01) |
| *A61B 5/117* | (2016.01) |
| *G06F 3/0488* | (2013.01) |
| *G06F 16/70* | (2019.01) |
| *H04N 5/247* | (2006.01) |
| *G01S 13/38* | (2006.01) |
| *G01S 13/88* | (2006.01) |
| *G01S 5/16* | (2006.01) |
| *G01S 11/14* | (2006.01) |
| *G10L 17/00* | (2013.01) |
| *G01S 13/86* | (2006.01) |
| *G06N 3/04* | (2006.01) |
| *G08B 29/18* | (2006.01) |

(52) U.S. Cl.
CPC .......... *A61B 5/1113* (2013.01); *A61B 5/7475* (2013.01); *G01S 5/18* (2013.01); *G01S 5/28* (2013.01); *G01S 13/726* (2013.01); *G06F 1/324* (2013.01); *G06F 1/3206* (2013.01); *G06F 1/3231* (2013.01); *G06F 3/011* (2013.01); *G06F 3/017* (2013.01); *G06F 3/0304* (2013.01); *G06F 3/0482* (2013.01); *G06F 3/04842* (2013.01); *G06F 3/167* (2013.01); *G06F 17/271* (2013.01); *G06F 17/279* (2013.01); *G06F 21/32* (2013.01); *G06F 21/35* (2013.01); *G06K 9/00214* (2013.01); *G06K 9/00255* (2013.01); *G06K 9/00261* (2013.01); *G06K 9/00288* (2013.01); *G06K 9/00295* (2013.01); *G06K 9/00342* (2013.01); *G06K 9/00362* (2013.01); *G06K 9/00711* (2013.01); *G06K 9/00973* (2013.01); *G06K 9/6254* (2013.01); *G06K 9/6255* (2013.01); *G06K 9/6289* (2013.01); *G06K 9/6296* (2013.01); *G06N 5/025* (2013.01); *G06N 5/047* (2013.01); *G06N 20/00* (2019.01); *G06T 7/248* (2017.01); *G06T 7/292* (2017.01); *G06T 7/60* (2013.01); *G06T 7/70* (2017.01); *G06T 7/74* (2017.01); *G07C 9/00111* (2013.01); *G08B 13/1427* (2013.01); *G10L 15/02* (2013.01); *G10L 15/063* (2013.01); *G10L 15/08* (2013.01); *G10L 15/18* (2013.01); *G10L 15/1815* (2013.01); *G10L 15/1822* (2013.01); *G10L 15/19* (2013.01); *G10L 15/22* (2013.01); *G10L 15/24* (2013.01); *G10L 15/26* (2013.01); *G10L 15/28* (2013.01); *G10L 15/32* (2013.01); *G10L 17/04* (2013.01); *G10L 17/08* (2013.01); *G10L 25/51* (2013.01); *H04L 51/02* (2013.01); *H04L 63/102* (2013.01); *H04L 67/12* (2013.01); *H04L 67/22* (2013.01); *H04N 5/23219* (2013.01); *H04N 5/332* (2013.01); *H04N 7/181* (2013.01); *H04N 7/188* (2013.01); *H04N 21/231* (2013.01); *H04N 21/42203* (2013.01); *H04N 21/44218* (2013.01); *H04N 21/44222* (2013.01); *H04R 1/406* (2013.01); *H04R 3/005* (2013.01); *H04W 4/029* (2018.02); *H04W 4/33* (2018.02); *A61B 5/05* (2013.01); *A61B 5/1118* (2013.01); *G01S 5/16* (2013.01); *G01S 11/14* (2013.01); *G01S 13/38* (2013.01); *G01S 13/867* (2013.01); *G01S 13/888* (2013.01); *G06F 3/0488* (2013.01); *G06F 16/70* (2019.01); *G06F 2203/0381* (2013.01); *G06F 2221/2111* (2013.01); *G06K 2209/09* (2013.01); *G06N 3/0445* (2013.01); *G06T 2207/10016* (2013.01); *G06T 2207/10024* (2013.01); *G06T 2207/20101* (2013.01); *G06T 2207/30196* (2013.01); *G06T 2207/30201* (2013.01); *G06T 2207/30204* (2013.01); *G06T 2207/30232* (2013.01); *G07C 9/00134* (2013.01); *G08B 29/186* (2013.01); *G10L 17/00* (2013.01); *G10L 2015/0635* (2013.01); *G10L 2015/088* (2013.01); *G10L 2015/223* (2013.01); *G10L 2015/225* (2013.01); *G10L 2015/228* (2013.01); *H04N 5/247* (2013.01); *Y02D 10/126* (2018.01); *Y02D 10/173* (2018.01)

(58) Field of Classification Search
CPC ........... G06K 9/00295; G06K 9/00711; G06K
9/00973; G06K 9/6254; G06K 9/6255;
G06K 9/6289; G06K 9/6296; G06T
7/292; G06T 7/74; G06T 7/248; G06T
7/70; G06T 7/60; A61B 5/0205; A61B
5/0507; G06F 1/3206; G06F 1/3231;
G06F 1/324; G06F 3/011; G06F 3/017;
G06F 3/0304; G06F 3/0482; G06F 3/167;
G06F 17/271; G06F 17/279; G06F 21/32;
G06F 21/35; H04N 7/181; H04N 7/183;
H04N 7/185; H04N 7/186; H04N 7/188
USPC ........................................................ 382/103
See application file for complete search history.

(56) References Cited

U.S. PATENT DOCUMENTS

| | | |
|---|---|---|
| 6,332,122 B1 | 12/2001 | Ortega et al. |
| 6,442,524 B1 | 8/2002 | Ecker et al. |
| 6,477,500 B2 | 11/2002 | Maes |
| 6,496,799 B1 | 12/2002 | Pickering |
| 6,574,601 B1 | 6/2003 | Brown et al. |
| 6,728,679 B1 | 4/2004 | Strubbe et al. |
| 6,816,730 B2 | 11/2004 | Davies et al. |
| 6,873,953 B1 | 3/2005 | Lennig |
| 7,019,749 B2 | 3/2006 | Guo et al. |
| 7,050,110 B1 | 5/2006 | Lienhart et al. |
| 7,330,566 B2 | 2/2008 | Cutler |
| 7,475,010 B2 | 1/2009 | Chao |
| 7,610,365 B1 | 10/2009 | Kraft et al. |
| 7,716,056 B2 | 5/2010 | Weng et al. |
| 7,803,050 B2 | 9/2010 | Mao et al. |
| 8,139,945 B1 | 3/2012 | Amir et al. |
| 8,165,087 B2 | 4/2012 | Panabaker |
| 8,170,875 B2 | 5/2012 | Hetherington et al. |
| 8,213,689 B2 | 7/2012 | Yagnik et al. |
| 8,265,252 B2 | 9/2012 | Ducheneaut et al. |
| 8,326,627 B2 | 12/2012 | Kennewick et al. |
| 8,340,975 B1 | 12/2012 | Rosenberger |
| 8,374,879 B2 | 2/2013 | Falcon et al. |
| 8,453,402 B2 | 6/2013 | Huang |
| 8,457,959 B2 | 6/2013 | Kaiser |
| 8,543,402 B1 | 9/2013 | Ma |
| 8,639,762 B2 | 1/2014 | Rasmussen et al. |
| 8,644,842 B2 | 2/2014 | Arrasvuori et al. |
| 8,712,758 B2 | 4/2014 | Crouch et al. |
| 8,752,145 B1 | 6/2014 | Dotan et al. |
| 8,762,150 B2 | 6/2014 | Edgington et al. |
| 8,762,156 B2 | 6/2014 | Chen |
| 8,779,965 B2 | 7/2014 | Sentelle et al. |
| 8,805,691 B2 | 8/2014 | Genly |
| 8,861,924 B2 | 10/2014 | Meads et al. |
| 8,903,128 B2 | 12/2014 | Shet et al. |
| 8,913,103 B1 | 12/2014 | Sargin et al. |
| 8,942,986 B2 | 1/2015 | Cheyer et al. |
| 8,949,359 B2 | 2/2015 | Rasmussen et al. |
| 9,037,601 B2 | 5/2015 | Palay |
| 9,085,303 B2 | 7/2015 | Wolverton et al. |
| 9,119,512 B2 | 9/2015 | Martins, Jr. et al. |
| 9,171,542 B2 | 10/2015 | Gandrabur et al. |
| 9,230,544 B2 | 1/2016 | Kwon et al. |
| 9,268,406 B2 | 2/2016 | Geisner et al. |
| 9,300,925 B1 * | 3/2016 | Zhang .................... H04N 7/181 |
| 9,307,355 B2 | 4/2016 | Nehrenz et al. |
| 9,311,932 B2 | 4/2016 | Carter |
| 9,318,105 B1 | 4/2016 | Khosla |
| 9,348,990 B2 | 5/2016 | Chuaprasert et al. |
| 9,368,114 B2 | 6/2016 | Larson et al. |
| 9,378,740 B1 | 6/2016 | Rosen et al. |
| 9,380,177 B1 | 6/2016 | Rao et al. |
| 9,389,681 B2 | 7/2016 | Sankar et al. |
| 9,412,392 B2 | 8/2016 | Lindahl |
| 9,424,840 B1 | 8/2016 | Hart et al. |
| 9,466,286 B1 | 10/2016 | Hart et al. |
| 9,495,331 B2 | 11/2016 | Govrin et al. |
| 9,495,613 B2 | 11/2016 | Holz et al. |
| 9,507,977 B1 | 11/2016 | Mor et al. |
| 9,508,341 B1 | 11/2016 | Parlikar et al. |
| 9,514,227 B1 | 12/2016 | Garrett et al. |
| 9,558,749 B1 | 1/2017 | Secker-Walker et al. |
| 9,576,574 B2 | 2/2017 | van Os |
| 9,622,059 B2 | 4/2017 | Bouzid et al. |
| 9,626,352 B2 | 4/2017 | Allen et al. |
| 9,633,652 B2 | 4/2017 | Kurniawati et al. |
| 9,749,583 B1 | 8/2017 | Fineberg et al. |
| 9,761,055 B2 | 9/2017 | Miller |
| 9,767,616 B2 | 9/2017 | Miller |
| 9,842,299 B2 | 12/2017 | Stolarz et al. |
| 9,898,250 B1 | 2/2018 | Williams et al. |
| 9,965,247 B2 | 5/2018 | Jarvis et al. |
| 10,178,301 B1 | 1/2019 | Welbourne et al. |
| 2003/0103647 A1 | 6/2003 | Rui et al. |
| 2003/0131064 A1 | 7/2003 | Bell et al. |
| 2005/0182627 A1 | 8/2005 | Tanaka et al. |
| 2005/0216264 A1 | 9/2005 | Attwater et al. |
| 2005/0225427 A1 | 10/2005 | Bell et al. |
| 2005/0285774 A1 | 12/2005 | Wittenberg et al. |
| 2006/0028552 A1 | 2/2006 | Aggarwal et al. |
| 2007/0024487 A1 | 2/2007 | Zemany et al. |
| 2007/0100480 A1 | 5/2007 | Sinclair et al. |
| 2007/0152157 A1 | 7/2007 | Page |
| 2007/0198245 A1 | 8/2007 | Kamatani et al. |
| 2007/0271086 A1 | 11/2007 | Peters et al. |
| 2008/0030345 A1 | 2/2008 | Austin et al. |
| 2008/0071547 A1 | 3/2008 | Prieto et al. |
| 2008/0077015 A1 | 3/2008 | Boric-Lubecke et al. |
| 2008/0195387 A1 | 8/2008 | Zigel et al. |
| 2008/0288251 A1 | 11/2008 | Cooper et al. |
| 2009/0066690 A1 | 3/2009 | Harrison |
| 2009/0303342 A1 | 12/2009 | Corcoran et al. |
| 2009/0319269 A1 | 12/2009 | Aronowitz |
| 2010/0100851 A1 | 4/2010 | Clark et al. |
| 2010/0179813 A1 | 7/2010 | Summerfield et al. |
| 2010/0195906 A1 | 8/2010 | Uliyar et al. |
| 2011/0010170 A1 | 1/2011 | Burns et al. |
| 2011/0184735 A1 | 7/2011 | Flaks et al. |
| 2011/0298967 A1 | 12/2011 | Clavin et al. |
| 2012/0026335 A1 | 2/2012 | Brown et al. |
| 2012/0265535 A1 | 10/2012 | Bryant-rich et al. |
| 2012/0268604 A1 | 10/2012 | Tree |
| 2013/0110519 A1 | 5/2013 | Cheyer et al. |
| 2013/0117377 A1 | 5/2013 | Miller |
| 2013/0212501 A1 | 8/2013 | Anderson et al. |
| 2013/0253936 A1 | 9/2013 | Harvey |
| 2013/0342568 A1 | 12/2013 | Ambrus et al. |
| 2014/0033071 A1 | 1/2014 | Gruber et al. |
| 2014/0067679 A1 | 3/2014 | O'Reilly et al. |
| 2014/0180629 A1 | 6/2014 | Dokmanic et al. |
| 2014/0214421 A1 | 7/2014 | Shriberg et al. |
| 2014/0214429 A1 | 7/2014 | Pantel |
| 2014/0222422 A1 | 8/2014 | Sarikaya et al. |
| 2014/0244263 A1 | 8/2014 | Pontual et al. |
| 2014/0330569 A1 | 11/2014 | Kolavennu et al. |
| 2014/0341440 A1 | 11/2014 | Walch |
| 2015/0016642 A1 | 1/2015 | Walsh et al. |
| 2015/0019714 A1 | 1/2015 | Shaashua et al. |
| 2015/0025887 A1 | 1/2015 | Sidi et al. |
| 2015/0032456 A1 | 1/2015 | Wait |
| 2015/0102996 A1 | 4/2015 | Yim et al. |
| 2015/0138332 A1 | 5/2015 | Cheng et al. |
| 2015/0149179 A1 | 5/2015 | Korbecki |
| 2015/0149182 A1 | 5/2015 | Kalns et al. |
| 2015/0162000 A1 | 6/2015 | Di censo et al. |
| 2015/0172285 A1 | 6/2015 | Lo et al. |
| 2015/0249664 A1 | 9/2015 | Talhami et al. |
| 2015/0279368 A1 | 10/2015 | Contolini et al. |
| 2015/0340033 A1 | 11/2015 | Di fabbrizio et al. |
| 2015/0347114 A1 | 12/2015 | Yoon |
| 2015/0382047 A1 | 12/2015 | Van os et al. |
| 2016/0019889 A1 | 1/2016 | Alvarez guevara et al. |
| 2016/0086018 A1 | 3/2016 | Lemoff |
| 2016/0088043 A1 | 3/2016 | Jiang et al. |
| 2016/0092732 A1 | 3/2016 | Black |

(56) References Cited

U.S. PATENT DOCUMENTS

| | | | |
|---|---|---|---|
| 2016/0138247 A1 | 5/2016 | Conway et al. | |
| 2016/0148417 A1 | 5/2016 | Kim et al. | |
| 2016/0155443 A1 | 6/2016 | Khan et al. | |
| 2016/0173293 A1 | 6/2016 | Kennedy | |
| 2016/0179831 A1 | 6/2016 | Gruber et al. | |
| 2016/0187961 A1* | 6/2016 | Elibol | G06F 1/3293 |
| | | | 713/323 |
| 2016/0203002 A1 | 7/2016 | Kannan et al. | |
| 2016/0210411 A1 | 7/2016 | Mentis | |
| 2016/0217783 A1 | 7/2016 | Konuma et al. | |
| 2016/0225373 A1 | 8/2016 | Casado et al. | |
| 2016/0234595 A1 | 8/2016 | Goran et al. | |
| 2016/0234616 A1 | 8/2016 | Gateau | |
| 2016/0283185 A1 | 9/2016 | Mclaren et al. | |
| 2016/0342702 A1 | 11/2016 | Barve et al. | |
| 2016/0358598 A1 | 12/2016 | Williams et al. | |
| 2016/0360336 A1 | 12/2016 | Gross et al. | |
| 2016/0380929 A1 | 12/2016 | Katis et al. | |
| 2017/0013409 A1 | 1/2017 | Cerchio et al. | |
| 2017/0025124 A1 | 1/2017 | Mixter et al. | |
| 2017/0032021 A1 | 2/2017 | Watanachote | |
| 2017/0032787 A1 | 2/2017 | Dayal | |
| 2017/0039423 A1 | 2/2017 | Cork et al. | |
| 2017/0039602 A1 | 2/2017 | Shi-nash et al. | |
| 2017/0068423 A1 | 3/2017 | Napolitano et al. | |
| 2017/0078573 A1 | 3/2017 | Chen et al. | |
| 2017/0133011 A1 | 5/2017 | Chen et al. | |
| 2017/0140760 A1 | 5/2017 | Sachdev | |
| 2017/0185375 A1 | 6/2017 | Martel et al. | |
| 2017/0194000 A1 | 7/2017 | Itani et al. | |
| 2017/0230705 A1 | 8/2017 | Pardue et al. | |
| 2017/0236512 A1 | 8/2017 | Williams et al. | |
| 2017/0242651 A1 | 8/2017 | Lang et al. | |
| 2017/0249309 A1 | 8/2017 | Sarikaya | |
| 2017/0262472 A1 | 9/2017 | Goldenberg | |
| 2017/0278480 A1 | 9/2017 | Sung et al. | |
| 2017/0287490 A1 | 10/2017 | Biswal et al. | |
| 2017/0315208 A1 | 11/2017 | Sadr | |
| 2017/0351749 A1 | 12/2017 | Quirk et al. | |
| 2017/0359666 A1 | 12/2017 | Lyren et al. | |
| 2018/0047394 A1 | 2/2018 | Tian et al. | |
| 2018/0048768 A1 | 2/2018 | Spittle et al. | |
| 2018/0074785 A1 | 3/2018 | Ohmura | |
| 2018/0091782 A1* | 3/2018 | Bashkin | H04N 7/188 |
| 2018/0096696 A1 | 4/2018 | Mixter | |
| 2018/0158454 A1 | 6/2018 | Campbell et al. | |
| 2018/0199123 A1 | 7/2018 | Rao et al. | |
| 2018/0218080 A1 | 8/2018 | Krishnamurthy et al. | |
| 2018/0231653 A1 | 8/2018 | Pradeep et al. | |
| 2018/0232201 A1 | 8/2018 | Holtmann | |
| 2018/0232563 A1 | 8/2018 | Albadawi et al. | |
| 2018/0232571 A1 | 8/2018 | Bathiche et al. | |
| 2018/0232608 A1 | 8/2018 | Pradeep et al. | |
| 2018/0232645 A1 | 8/2018 | Finkelstein et al. | |
| 2018/0232662 A1 | 8/2018 | Solomon et al. | |
| 2018/0233132 A1 | 8/2018 | Herold et al. | |
| 2018/0233139 A1 | 8/2018 | Finkelstein et al. | |
| 2018/0233140 A1 | 8/2018 | Koishida et al. | |
| 2018/0233141 A1 | 8/2018 | Solomon et al. | |
| 2018/0233142 A1 | 8/2018 | Koishida et al. | |
| 2018/0233145 A1 | 8/2018 | Bathiche et al. | |
| 2018/0260680 A1 | 9/2018 | Finkelstein et al. | |
| 2018/0293221 A1 | 10/2018 | Finkelstein et al. | |
| 2019/0057703 A1 | 2/2019 | Zeinstra | |

FOREIGN PATENT DOCUMENTS

| | | |
|---|---|---|
| KR | 20070016280 A | 2/2007 |
| WO | 2007018523 A2 | 2/2007 |
| WO | 2010104772 A1 | 9/2010 |
| WO | 2013061268 A2 | 5/2013 |
| WO | 2015012449 A1 | 1/2015 |
| WO | 2016114922 A1 | 7/2016 |
| WO | 2016162678 A1 | 10/2016 |
| WO | 2016205419 A1 | 12/2016 |

OTHER PUBLICATIONS

"Using Multiple Alexa Devices", Retrieved From <<https://www.amazon.com/gp/help/customer/display.html?nodeId=202013740>>, Apr. 24, 2017, 2 Pages.

"Application Filed in U.S. Appl. No. 15/173,349", filed Jun. 3, 2016, 34 Pages.

"Application Filed in U.S. Appl. No. 15/395,961", filed Dec. 30, 2016, 79 Pages.

Ballan, et al., "Event Detection and Recognition for Semantic Annotation of Video", In Journal of Multimedia Tools and Applications, vol. 51, Issue 1, Nov. 10, 2010, pp. 279-302.

Beltagy, et al., "Improved Semantic Parsers for If-Then Statements", In Proceedings of the 54th Annual Meeting of be Association for Computational Linguistics, vol. 1, Aug. 7, 2016, pp. 726-736.

Sho, et al., "A Multi-Sensor Fusion System for Moving Object Detection and Tracking in Urban Driving Environments", In IEEE International Conference on Robotics & Automation, May 31, 2014, 8 Pages.

Fossard, et al., Between Anaphora and Deixis . . . The Resolution of the Demonstrative Noun Phrase "that N", In Journal of Language and Cognitive Processes, vol. 27, Issue 9, Nov. 2, 2011, 3 Pages.

Gebhart, Andrew, "How to bring Alexa into every room of your home", Retrieved From <<https://www.cnet.com/how-to/how-to-install-alexa-in-every-room-of-your-home/>>, Feb. 2, 2017, 8 Pages.

Goncalves, et al., "Assessing Users' Emotion At Interaction Time: A Multimodal Approach With Multiple Sensors", In Proceedings of Soft Computing, vol. 21, Issue 18, Mar. 21, 2016, 8 Pages.

Zotkin, et al., "Joint Audio-Visual Tracking Using Particle Filters", In EURASIP Journal on Applied Signal Processing, vol. 2002, Issue 1, Jan. 2002, pp. 1154-1164.

Huijbregts, et al., "Speech Overlap Detection in a Two-Pass Speaker Diarization System", In Proceedings of 10th Annual Conference of the International Speech Communication, Sep. 6, 2009, pp. 1063-1066.

Kabadjov, Mijail Alexandrov., "A Comprehensive Evaluation of Anaphora Resolution and Discourse-new Classification", In thesis of University of Essex, May 2007, 266 Pages.

Kang, et al., "Detection and Tracking of Moving Objects from Overlapping EO and IR Sensors", In Conference on Computer Vision and Pattern Recognition Workshop, Jun. 27, 2004, 6 Pages.

Liu, et al., "Reliable Multiple Object Tracking under Heavy Occlusions", In Intelligence Information Processing and Trusted Computing (IPTC), 2010 International Symposium., Oct. 28, 2010, 3 Pages.

MK, et al., "Ambiguities in Natural Language Processing", In International Journal of Innovative Research in Computer and Communication Engineering, vol. 2, Special Issue 5, Oct. 2014, pp. 392-394.

Pan, et al., "Robust Occlusion Handling in Object Tracking", In IEEE Conference on Computer Vision and Pattern Recognition, Jun. 17, 2007, 8 Pages.

Quirk, et al., "Language to Code: Learning Semantic Parsers for If-This-Then-That Recipes", In Proceedings of the 53rd Annual Meeting of the Association for Computational Linguistics, Jul. 26, 2015, pp. 878-888.

Boakye, et al., "Overlapped Speech Detection for Improved Speaker Diarization in Multiparty Meetings", In Proceedings of IEEE International Conference on Acoustics, Speech and Signal Processing, Mar. 31, 2008, 4 Pages.

Sinha, et al., "An Analysis Engine for Dependable Elicitation on Natural Language Use Case Description and its Application to Industrial Use Cases", In IBM Research Report, RC242712, Dec. 18, 2008, 12 Pages.

Toutanova, et al., "Compositional Learning of Embeddings for Relation Paths in Knowledge Bases and Text", In Proceedings of the

(56) References Cited

OTHER PUBLICATIONS

54th Annual Meeting of the Association for Computational Linguistics, Aug. 7, 2016, pp. 1434-1444.
Wagner, Martin, "Tracking with Multiple Sensors", By Faculty of Computer Science at the Technical University of Munich, Sep. 12, 2004, 202 Pages.
Wheeler, et al., Face Recognition at a Distance, In Publication of Springer, Jan. 2011, pp. 353-381.
Rizwan, et al., "Local Enhancement for Robust Face Detection in Poor SNR Images", In International Journal of Computer Science and Network Security, vol. 9, No. 6, Jun. 2009, pp. 93-96.
He, et al., "Sensor scheduling for target tracking: A Monte Carlo sampling approach", In Journal of Digital Signal Processing, vol. 16, Issue 5, Sep. 2006, pp. 533-545.
Goswami, et al., "A Reviewon Low Light Image Enhancement Using Image Processing Technique", In International Journal of Technical Research, vol. 5, Issue 1, Mar. 2016, pp. 60-62.
"Amazon Alexa's 'Follow-Up Mode' enables successive requests without trigger word", Retrieved from: https://appleinsider.com/articles/18/03/09/amazon-alexas-follow-up-mode-enables-successive-requests-without-trigger-word, Mar. 9, 2018, 7 Pages.
"Multiple Agents (each trained for different domain) for One Chat Bot?", Retrieved from: https://discuss.api.ai/t/multiple-agents-each-trained-for-different-domain-for-one-chat-bot/1002, Jul. 1, 2016, 1 Page.
"SARA: the Socially Aware Robot Assistant", Retrieved from: https://web.archive.org/web/20160707141922/http:/articulab.hcii.cs.cmu.edu:80/projects/sara/, Jul. 7, 2017, 10 Pages.
Arsikere, et al., "Computationally-efficient Endpointing Features for Natural Spoken Interaction with Personal-assistant Systems", In Proceedings of IEEE International Conference on Acoustics, Speech and Signal Processing, May 4, 2014, pp. 3241-3245.
Ferrer, et al., "Is the Speaker Done Yet? Faster and More Accurate End-of-Utterance Detection using Prosody", In Proceedings of the 7th International Conference on Spoken Language Processing, Sep. 16, 2002, pp. 2061-2064.
Kalal, et al., "Face-TLD: Tracking-Learning-Detection Applied to Faces", In Proceedings of 17th IEEE International Conference on Image Processing, Sep. 26, 2010, pp. 3789-3792.
Kozhaya, Joe, "10 Steps to Train an Effective Chatbot and its Machine Learning Models", Retrieved from: https://developer.ibm.com/dwblog/2016/10-steps-train-chat-bot-chatbot-machine-learning/, Dec. 12, 2016, 7 Pages.
Lacharite, Noelle, "Updated: Alexa Skills Kit Fact Template: Step-by-Step Guide to Build a Fact Skill", Retrieved from https://developer.amazon.com/blogs/post/Tx3DVGG0K0TPUGQ/New-Alexa-Skills-Kit-Template:-Step-by-Step-Guide-to-Build-a-Fact-Skill, Mar. 29, 2016, 33 Pages.
Li, Bo, "A Multiple-Camera System Calibration Toolbox Using a Feature Descriptor-based Calibration Pattern", In Proceedings of IEEE International Conference on Intelligent Robots and Systems, Nov. 3, 2013, pp. 1301-1307.
Mengusoglu, Erhan, "Confidence Measures for Speech/Speaker Recognition and Applications on Turkish LVCSR", Retrieved from https://web.archive.org/web/20040619044603/http://www.tcts.fpms.ac.be/publications/phds/mengusoglu/thesis_mengus.pdf, Apr. 20, 2004, 143 Pages.
Verma et al., "Face Detection and Tracking in a Video by Propagating Detection Probabilities", In Proceedings of IEEE Transactions on Pattern Analysis and Machine Intelligence, vol. 25, Issue 10, Oct. 1, 2003, pp. 1215-1228.
Panzarino, Matthew, "Here's An Actual 3D Indoor Map of a Room Captured With Google's Project Tango Phone", Retrieved From https://techcrunch.com/2014/02/21/heres-an-actual-3d-indoor-map-of-a-room-captured-with-googles-project-tango-phone/, Feb. 21, 2014, 6 Pages.
"International Search Report and Written Opinion Issued in PCT Application No. PCT/US2018/017139", dated May 8, 2018, 13 Pages.

"International Search Report and Written Opinion Issued in PCT Application No. PCT/US2018/017140", dated May 18, 2018, 12 Pages.
"International Search Report and Written Opinion Issued in PCT Application No. PCT/US2018/017506", dated May 4, 2018, 13 Pages.
"International Search Report and Written Opinion Issued in PCT Application No. PCT/US2018/017508", dated May 8, 2018, 13 Pages.
"International Search Report and Written Opinion Issued in PCT Application No. PCT/US2018/017509", dated May 11, 2018, 11 Pages.
"International Search Report and Written Opinion Issued in PCT Application No. PCT/US2018/017510", dated Apr. 20, 2018, 14 Pages.
"International Search Report and Written Opinion Issued in PCT Application No. PCT/US2018/017511", dated May 17, 2018, 12 Pages.
"International Search Report and Written Opinion Issued in PCT Application No. PCT/US2018/017512", dated May 4, 2018, 15 Pages.
"International Search Report and Written Opinion Issued in PCT Application No. PCT/US2018/017513", dated Apr. 12, 2018, 15 Pages.
"International Search Report and Written Opinion Issued in PCT Application No. PCT/US2018/017514", dated May 17, 2018, 12 Pages.
"International Search Report and Written Opinion Issued in PCT Application No. PCT/US2018/017515", dated May 9, 2018, 12 Pages.
"International Search Report and Written Opinion Issued in PCT Application No. PCT/US2018/017517", dated May 11, 2018, 12 Pages.
Porcheron, et al., "Do Animals Have Accents?": Talking with Agents in Multi-Party Conversation, In Proceedings of the ACM Conference on Computer-Supported Cooperative Work and Social Computing, Feb. 25, 2017, 14 Pages.
Pullen, John Patrick., "Amazon Echo Tip: How to Add Multiple Users ! Time", Retrieved from http://time.com/4668359/amazon-echo-alexa-multiple-accounts/, Feb. 13, 2017, 3 Pages.
Xiang, Li, "Improving Knowledge Base Population With Information Extraction", A Thesis Submitted in Partial fulfillment of the Requirements of the University of New York for the Degree of Doctor of Philosophy, May 2016, 131 Pages.
Yamamoto, S, et al., "Algorithm Optimizations for Low-Complexity Eye Tracking", In Proceedings of IEEE International Conference on Systems, Man, and Cybernetics, Oct. 2009, pp. 18-22.
Yun-Nung, Chen, "Unsupervised Learning and Modeling of Knowledge and Intent for Spoken Dialogue Systems", Proceedings of the Annual Meeting of the Association for Computational Linguistics, Jul. 28, 2015, 8 Pages.
Zhang, et al., "A Joint Model of Intent Determination and Slot Filling for Spoken Language Understanding", In Proceedings of the 25th International Joint Conference on Artificial Intelligence, Jul. 9, 2016, pp. 2993-2999.
"Non Final Office Action Issued in U.S. Appl. No. 15/640,251", dated Oct. 15, 2018, 22 Pages.
"Non Final Office Action Issued in U.S. Appl. No. 15/646,871", dated Dec. 19, 2018, 22 Pages.
"Non Final Office Action Issued in U.S. Appl. No. 15/656,994", dated Jan. 22, 2019, 8 Pages.
"Non Final Office Action Issued in U.S. Appl. No. 15/657,031", dated Oct. 5, 2018, 16 Pages.
"Non-Final Office Action Issued in U.S. Appl. No. 15/657,822", dated Feb. 21, 2019, 25 Pages.
"Non Final Office Action Issued in U.S. Appl. No. 15/832,656", dated Feb. 7, 2019, 8 Pages.
"Non Provisional Application Filed in U.S. Appl. No. 15/885,518", filed Jan. 31, 2018, 40 Pages.
"Final Office Action Issued in U.S. Appl. No. 15/640,251", dated Apr. 2, 2019, 22 Pages.

(56) References Cited

OTHER PUBLICATIONS

Yu, et al., "Smart Meeting Systems: A Survey of State of the Art and Open Issues", In the Proceedings of ACM Computing Surveys, vol. 42, No. 2, Mar. 5, 2010, 20 Pages.
"International Search Report & Written Opinion for PCT Patent Application No. PCT/US2018/062384", dated Feb. 15, 2019, 12 Pages.
Moattar, et al., "A Review on Speaker Diarization Systems and Approaches", In the Publication of Speech Communication, vol. 54, Issue 10, Dec. 12, 2010, 39 Pages.
Miro, et al., "Speaker Diarization: A review of Recent Research", In the Proceedings of IEEE Transactions on Audio, Speech and Language Processing, vol. 20, Issue 2, Feb. 1, 2012, 15 Pages.
"Final Office Action Issued in U.S. Appl. No. 15/646,871", dated Apr. 19, 2019, 22 Pages.
"Non Final Office Action Issued in U.S. Appl. No. 15/682,425", dated May 6, 2019, 12 Pages.
"Non Final Office Action Issued in U.S. Appl. No. 15/682,407", dated Jun. 26, 2019, 15 Pages.
"International Search Report and Written Opinion Issued in PCT Application No. PCT/US2019/022836", dated Jun. 24, 2019, 15 Pages.
Constine, Jose, "Instagram launches selfie filters, copying the last big Snapchat feature", Retrieved from https://techcrunch.com/2017/05/16/instagram-face-filters/, May 16, 2017, 8 Pages.
"International Search Report and Written Opinion Issued in PCT Application No. PCT/US2019/029558", dated Jun. 28, 2019, 10 Pages.

\* cited by examiner

COMPUTATIONALLY-EFFICIENT HUMAN-IDENTIFYING SMART ASSISTANT COMPUTER

CROSS REFERENCE TO RELATED APPLICATIONS

This application claims priority to U.S. Provisional Patent Application No. 62/459,020 filed Feb. 14, 2017, and to U.S. Provisional Patent Application No. 62/482,165 filed Apr. 5, 2017, the entirety of which are hereby incorporated herein by reference.

BACKGROUND

Interacting with computing systems via natural interactions, such as one or more of voice recognition, text, gesture recognition, motion detection, gaze detection, intent recognition, brain activity assessment, text, the state of a home automated device, etc., enables natural user interface experiences. As the volume of digital information and the numbers of computing devices increase, managing such natural user interaction interfaces to provide positive user experiences can prove challenging.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

A computationally-efficient method for a smart assistant computer to track a human includes receiving data from one or more sensors configured to monitor a physical environment. The data is computer-analyzed to recognize presence of a human in the physical environment, and upon confirming an identity of the human, a first level of computational resources of the smart assistant computer is dedicated to track the human. Upon failing to confirm the identity of the human while a known user is present, a second level of computational resources of the smart assistant computer, greater than the first level, is dedicated to determine the identity of the human. Upon failing to confirm the identity of the human while the known user is absent, a third level of computational resources of the smart assistant computer, is dedicated to determine the identity of the human.

DETAILED DESCRIPTION

The present disclosure relates generally to systems, methods and logical constructs for providing intelligent assistance to users. In some examples, a variety of sensor data may be utilized to intelligently determine the content and/or timing of messages communicated to users and/or the performance of actions. Such data may be processed to generate identity, location/position, status/activity, and/or other information related to one or more entities within range of a sensor. Statistical probabilities based on current and past data may be utilized to generate confidence values associated with entity information. Such information can, in some cases, be used to provide numerous security features, such as identifying unrecognized humans in a physical environment. Furthermore, the human identification can be performed in a computationally-efficient manner.

Figure 1:
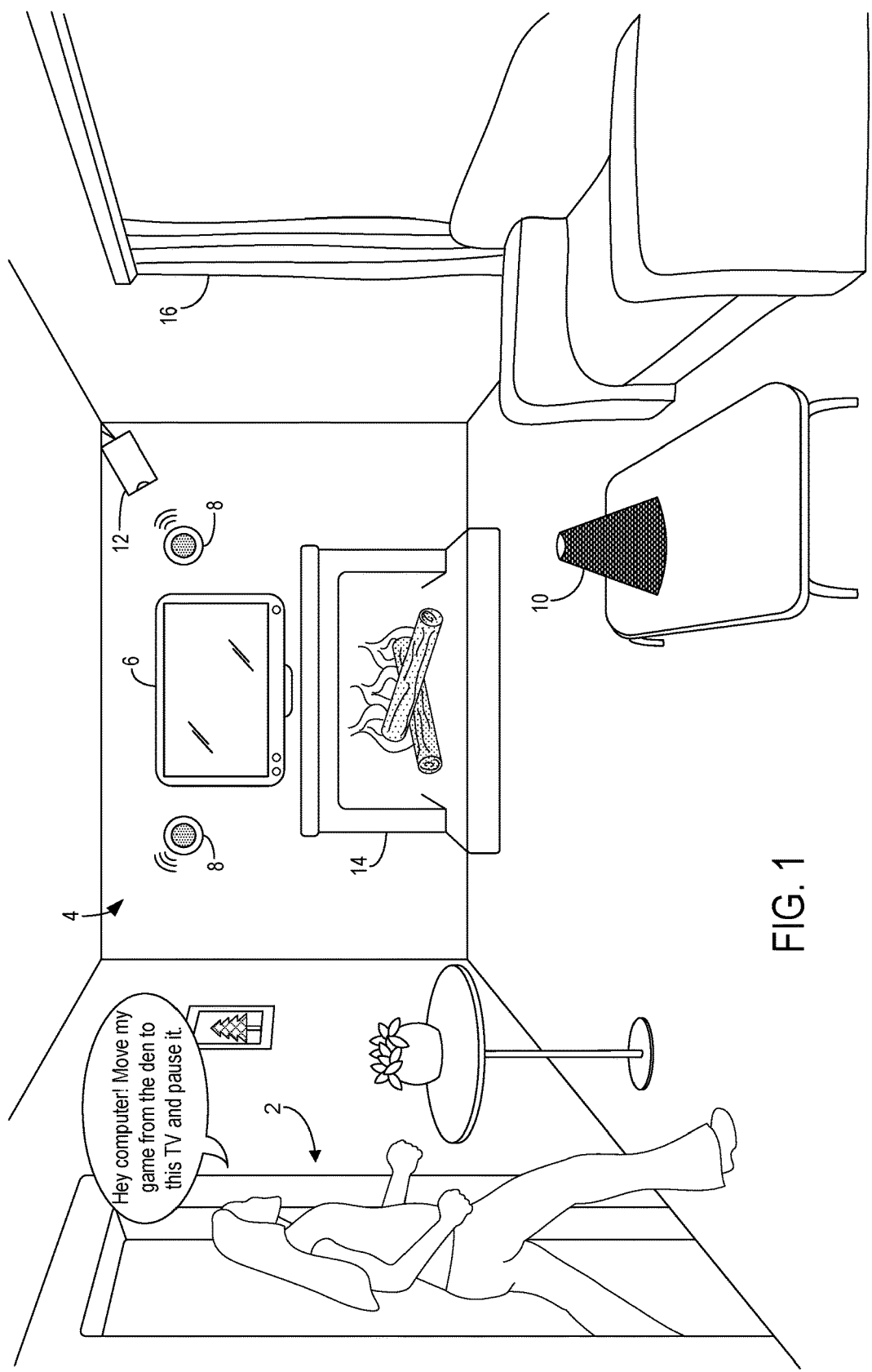
FIG. 1 shows an example environment with a smart assistant computer in the form of an all-in-one computing device according to an example of the present disclosure.

FIG. 1 illustrates a human 2 entering a living room 4 with one example of a smart assistant computer in the form of an all-in-one computing device 10. As described in more detail below, in some examples computing device 10 may be configured to receive and process natural language inputs. A user may utilize the smart assistant computer for myriad functions. For example, the user may provide natural language input to ask the smart assistant computer to perform a variety of tasks, such as transferring an instance of a computer game from one device to another. In another example, such a transfer may be performed programmatically without input from the user. For example, computing device 10 may utilize sensor data, such as audio and/or video data, for example received from a camera 12, to detect when the user moves to another room and is looking at or "engaged" with another device. Using this data, computing device 10 may automatically transfer the instance of the computer game to the other device.

The user may ask the system for information about a wide range of topics, such as the weather, personal calendar events, movie show times, etc. In some examples, the smart assistant computer also may be configured to control elements in the living room 4, such as a television 6, speakers 8 of a music system, a gas fireplace 14, or motorized curtains 16.

The smart assistant computer also may be utilized to receive and store messages and/or reminders to be delivered at an appropriate future time. Using data received from sensors, the smart assistant computer may track and/or communicate with one or more users or other entities.

In some examples, the computing device 10 may be operatively connected with one or more other computing devices using a wired connection, or may employ a wireless connection via Wi-Fi, Bluetooth, or any other suitable wireless communication protocol. For example, the computing device 10 may be communicatively coupled to one or more other computing devices via a network. The network may take the form of a local area network (LAN), wide area network (WAN), wired network, wireless network, personal area network, or a combination thereof, and may include the Internet. Additional details regarding components and computing aspects of the computing device 10 are described in more detail below with reference to FIG. 12.

Figure 9:
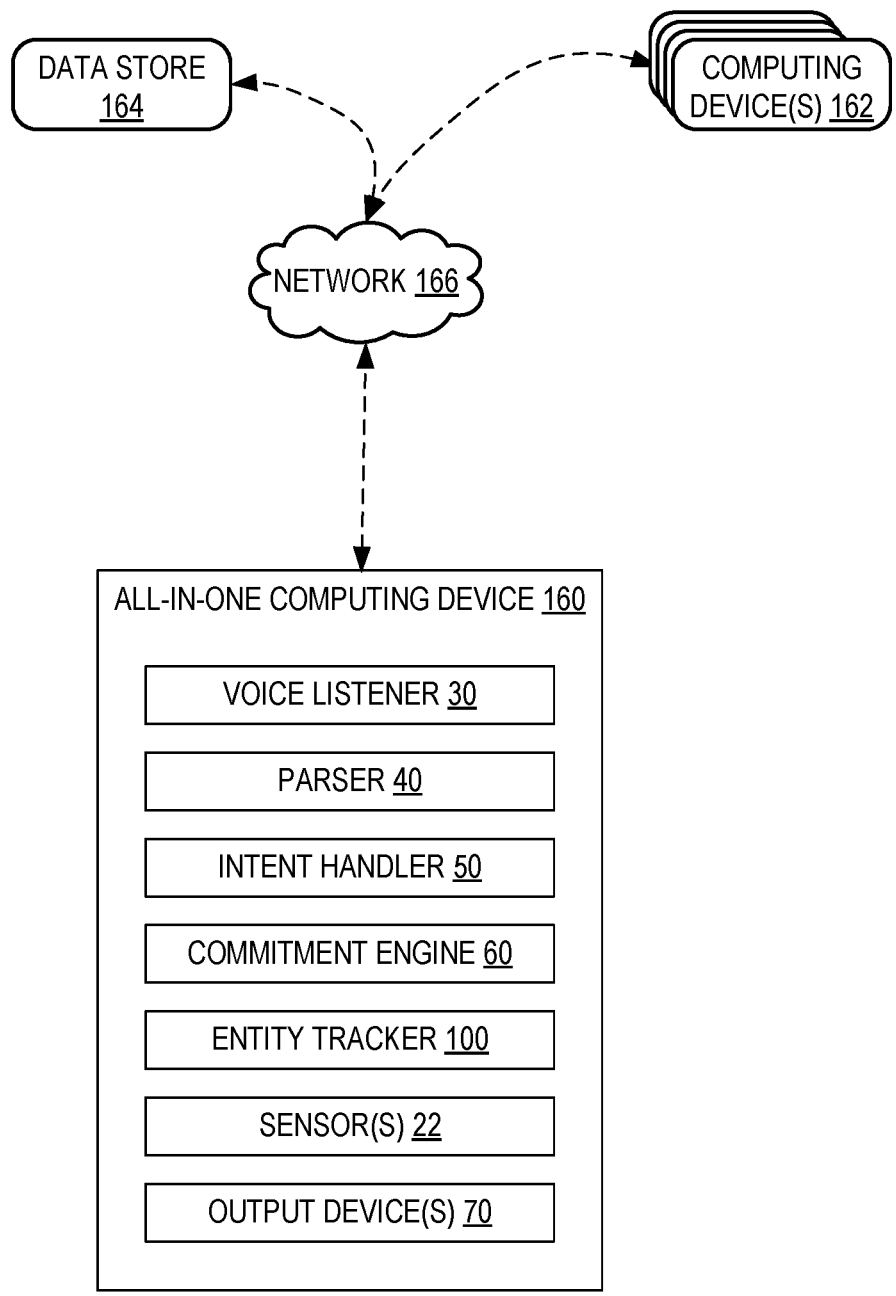
FIG. 9 schematically shows an all-in-one computing device that implements a smart assistant computer according to examples of the present disclosure.
Figure 10:
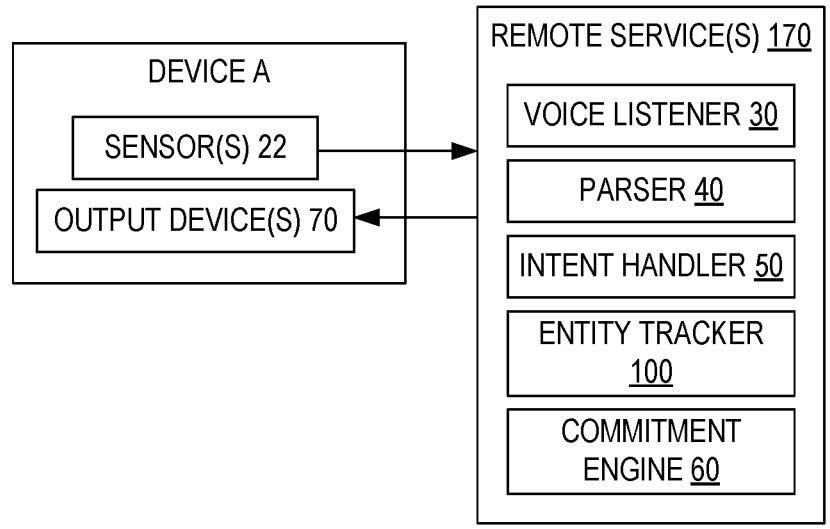
FIG. 10 schematically shows an example implementation in which one or more remote services perform functionality of the smart assistant computer according to examples of the present disclosure.
Figure 11:
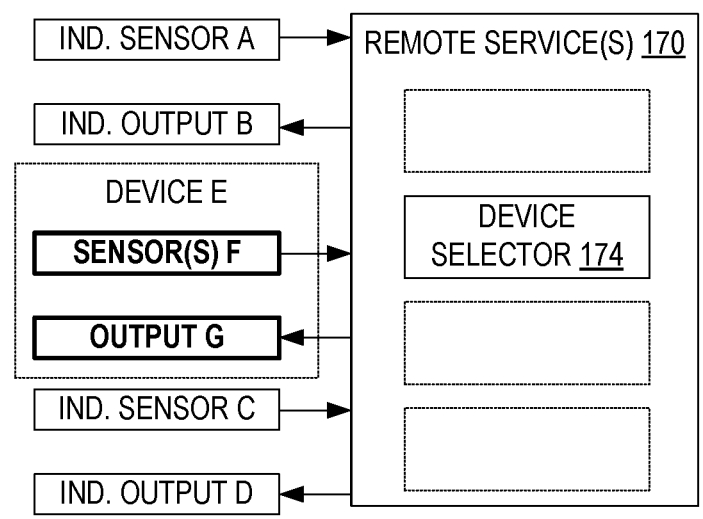
FIG. 11 schematically shows another example implementation in which one or more remote services perform functionality of smart assistant computer according to examples of the present disclosure.

It will be appreciated that the computing device 10 of FIG. 1 is merely one example implementation of the smart assistant computer of the present disclosure. Additional example implementations across two or more devices are illustrated in FIGS. 9-11 and described in more detail below.

Figure 2:
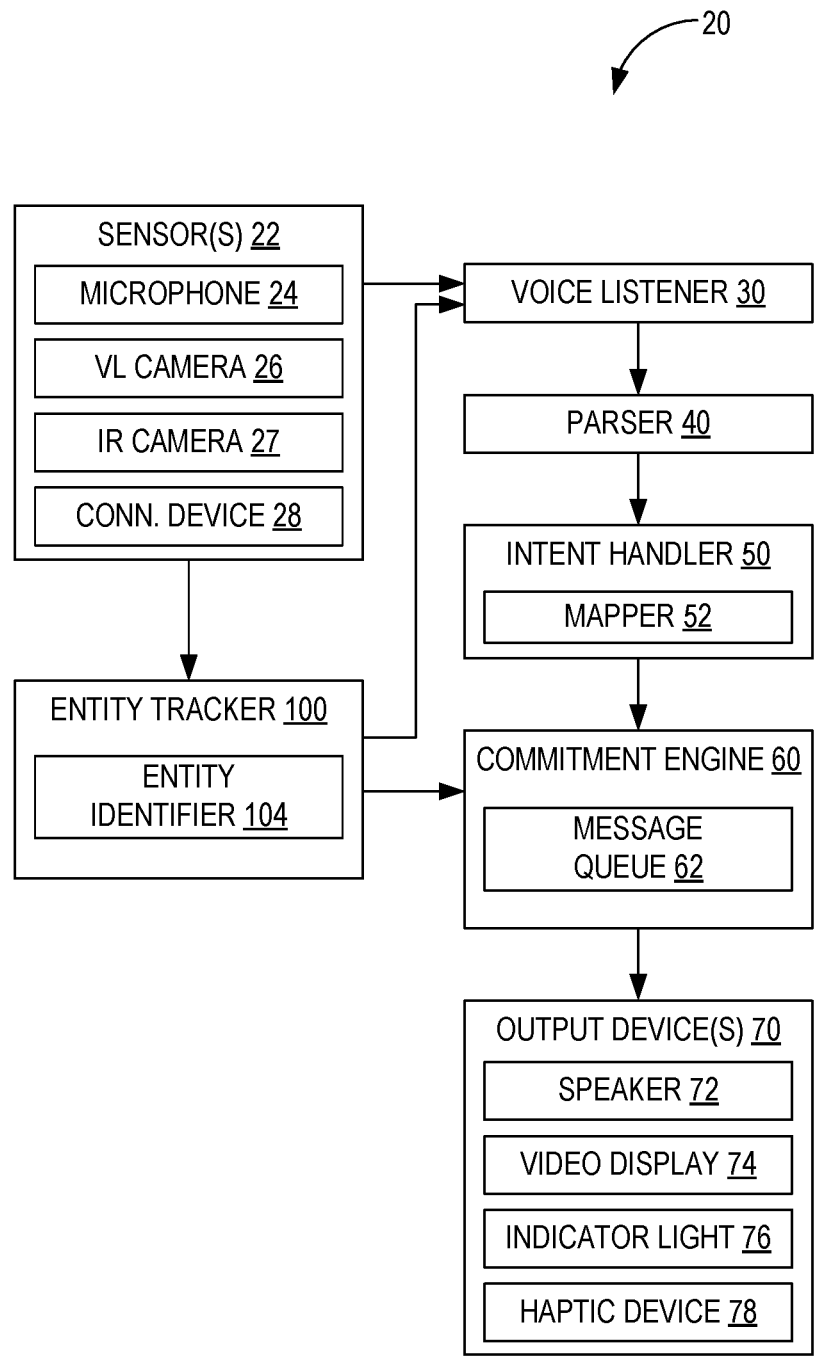
FIG. 2 schematically shows an example logical architecture for implementing a smart assistant computer according to an example of the present disclosure.

FIG. 2 shows an example logical architecture for implementing a smart assistant computer 20 capable of recognizing and responding to natural language inputs according to examples of the present disclosure. As described in more detail below, in various examples the system 20 may be implemented in a single computing device, across two or more devices, in a cloud-supported network, and in combinations of the foregoing.

In this example the smart assistant computer 20 includes at least one sensor 22, an entity tracker 100, a voice listener 30, a parser 40, an intent handler 50, a commitment engine 60, and at least one output device 70. In some examples the sensors 22 may include one or more microphones 24, visible light cameras 26, infrared cameras 27, and connectivity devices 28, such as Wi-Fi or Bluetooth modules. In some examples sensor(s) 22 may comprise stereoscopic and/or depth cameras, head trackers, eye trackers, accelerometers, gyroscopes, gaze detection devices, electric-field sensing componentry, GPS or other location tracking devices, temperature sensors, device state sensors, and/or any other suitable sensor.

The entity tracker 100 is configured to detect entities and their activities, including people, animals, or other living things, as well as non-living objects. Entity tracker 100 includes an entity identifier 104 that is configured to recognize individual users and/or non-living objects. Voice listener 30 receives audio data and utilizes speech recognition functionality to translate spoken utterances into text. Voice listener 30 also may assign confidence value(s) to the translated text, and may perform speaker recognition to determine an identity of the person speaking, as well as assign probabilities to the accuracy of such identifications. Parser 40 analyzes text and confidence values received from voice listener 30 to derive user intentions and generate corresponding machine-executable language.

Intent handler 50 receives machine-executable language representing user intentions from the parser 40, and resolves missing and ambiguous information to generate commitments. Commitment engine 60 stores commitments from the intent handler 50. At a contextually appropriate time, the commitment engine may deliver one or more messages and/or execute one or more actions that are associated with one or more commitments. Commitment engine 60 may store messages in a message queue 62 or cause one or more output devices 70 to generate output. The output devices 70 may comprise one or more of speaker(s) 72, video display(s) 74, indicator light(s) 76, haptic device(s) 78, and/or other suitable output devices. In other examples, output devices 70 may comprise one or more other devices or systems, such as home lighting, thermostats, media programs, door locks, etc., that may be controlled via actions executed by the commitment engine 60.

In different examples the voice listener 30, parser 40, intent handler 50, commitment engine 60, and/or entity tracker 100 may be embodied in software that is stored in memory and executed by one or more processors of a computing device. In some implementations, specially programmed logic processors may be utilized to increase the computational efficiency and/or effectiveness of the smart assistant computer. Additional details regarding the components and computing aspects of computing devices that may store and execute these modules are described in more detail below with reference to FIG. 12.

With reference again to FIG. 2, in some examples the voice listener 30 and/or commitment engine 60 may receive context information including associated confidence values from entity tracker 100. As described in more detail below, entity tracker 100 may determine an identity, position, and/or current status of one or more entities within range of one or more sensors, and may output such information to one or more other modules, such as voice listener 30, commitment engine 60, etc. In some examples, entity tracker 100 may interpret and evaluate sensor data received from one or more sensors, and may output context information based on the sensor data. Context information may include the entity tracker's guesses/predictions as to the identity, position, and/or status of one or more detected entities based on received sensor data. In some examples, the guesses/predictions may additionally include a confidence value defining the statistical likelihood that the information is accurate.

Figure 3:
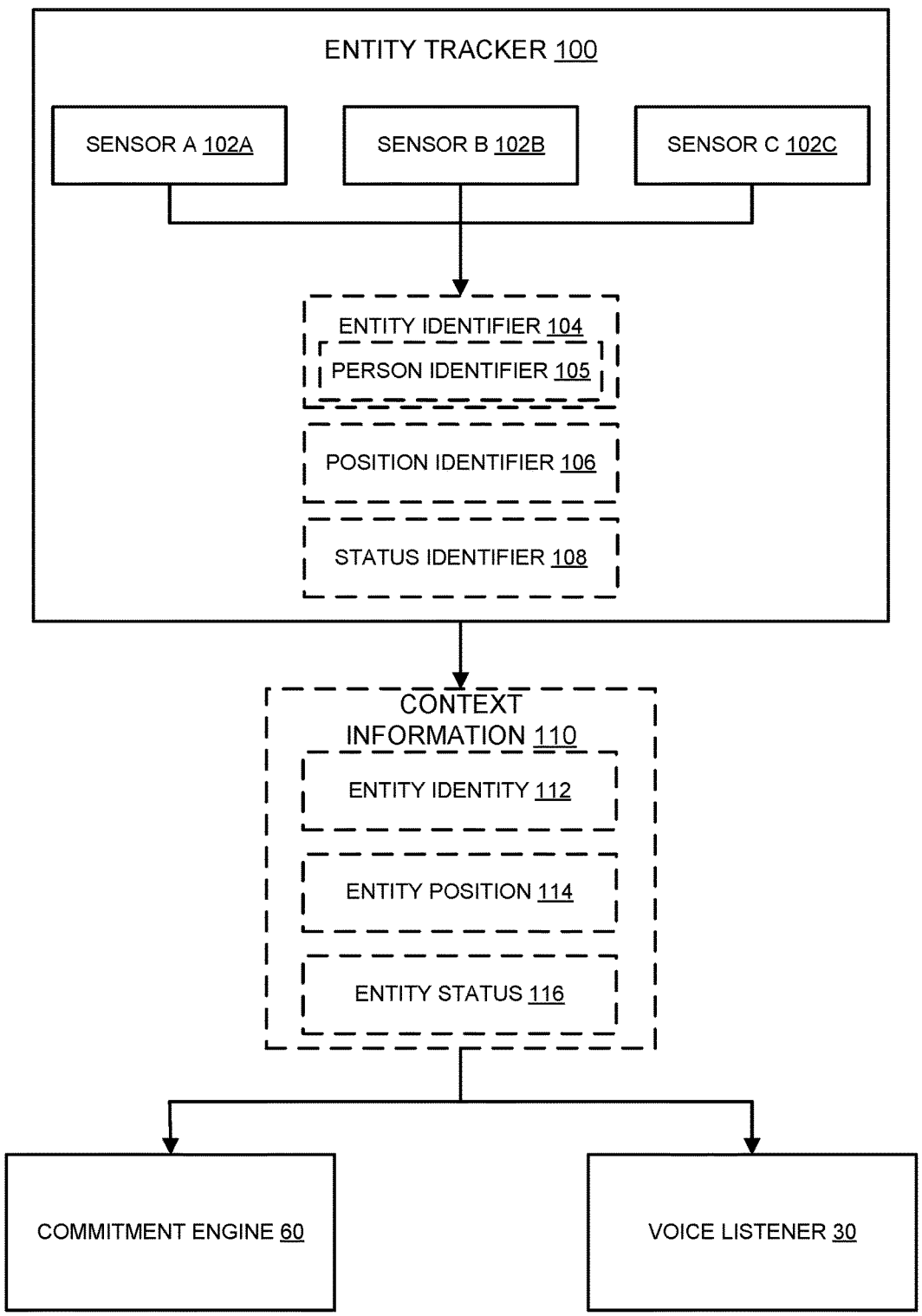
FIG. 3 schematically shows an entity tracker that may determine an identity, position, and/or current status of one or more entities according to examples of the present disclosure.

FIG. 3 schematically illustrates an example entity tracker 100 that may comprise a component of the smart assistant computer 20. Entity tracker 100 may be used to determine an identity, position, and/or current status of one or more entities within range of one or more sensors. Entity tracker 100 may output such information to one or more other modules of smart assistant computer 20, such as the commitment engine 60, voice listener 30, etc.

The word "entity" as used in the context of the entity tracker 100 may refer to people, animals, or other living things, as well as non-living objects. For example, the entity tracker may be configured to identify furniture, appliances, structures, landscape features, vehicles, and/or any other physical object, and determine the position/location and current status of such physical objects. In some cases, the entity tracker 100 may be configured to only identify people and not other living or non-living things. In such cases, the word "entity" may be synonymous with the word "person."

Entity tracker 100 receives sensor data from one or more sensors 102, such as sensor A 102A, sensor B 102B, and sensor C 102C, though it will be understood that an entity tracker may be used with any number and variety of suitable sensors. As examples, sensors usable with an entity tracker may include cameras (e.g., visible light cameras, UV cameras, IR cameras, depth cameras, thermal cameras), microphones, directional microphone arrays, pressure sensors, thermometers, motion detectors, proximity sensors, accelerometers, global positioning satellite (GPS) receivers, magnetometers, radar systems, lidar systems, environmental monitoring devices (e.g., smoke detectors, carbon monoxide detectors), barometers, health monitoring devices (e.g., electrocardiographs, sphygmomanometers, electroencephalograms), automotive sensors (e.g., speedometers, odometers, tachometers, fuel sensors), and/or any other sensors or devices that collect and/or store information pertaining to the identity, position, and/or current status of one or more people or other entities. In some examples, the entity tracker 100 may occupy a common device housing with one or more of the plurality of sensors 102, and/or the entity tracker and its associated sensors may be distributed across multiple devices configured to communicate via one or more network communications interfaces (e.g., Wi-Fi adapters, Bluetooth interfaces).

As shown in the example of FIG. 3, entity tracker 100 may include an entity identifier 104, a person identifier 105, a position (location) identifier 106, and a status identifier 108. In some examples, the person identifier 105 may be a specialized component of the entity identifier 100 that is particularly optimized for recognizing people, as opposed to other creatures and non-living things. In other cases, the person identifier 105 may operate separately from the entity identifier 104, or the entity tracker 100 may not include a dedicated person identifier.

Depending on the specific implementation, any or all of the functions associated with the entity identifier, person identifier, position identifier, and status identifier may be performed by the individual sensors 102A-102C. Though the present description generally describes the entity tracker 100 as receiving data from sensors, this does not require that the entity identifier 104, as well as other modules of the entity tracker, must be implemented on a single computing device that is separate and distinct from the plurality of sensors associated with the entity tracker. Rather, functions of the entity tracker 100 may be distributed amongst the plurality of sensors, or other suitable devices. For example, rather than sending raw sensor data to the entity tracker, individual sensors may be configured to attempt to identify entities that they detect, and report this identification to the entity tracker 100, and/or other modules of smart assistant computer 20. Furthermore, to simplify descriptions below, the term "sensor" is sometimes used to describe not only the physical measurement device (e.g., microphone or camera), but also the various logic processors configured and/or programmed to interpret signals/data from the physical measurement devices. For example, a "microphone" may be used to refer to the device that translates acoustic energy to an electrical signal, the analog-to-digital converter that converts the electrical signal to digital data, the on-board application-specific-integrated-circuit that pre-processes the digital data, and the downstream modules described herein (e.g., entity tracker 100, entity identifier 104, voice listener 30, or parser 40). As such, reference to a generic "sensor" or a particular sensor (e.g., "microphone" or "camera") should not be construed to mean only the physical measurement device, but also the cooperating modules/engines, which can be distributed across one or more computers.

Each of the entity identifier 104, person identifier 105, position identifier 106, and status identifier 108 is configured to interpret and evaluate sensor data received from the plurality of sensors 102, and to output context information 110 based on the sensor data. Context information 110 may include the entity tracker's guesses/predictions as to an identity, position, and/or status of one or more detected entities based on received sensor data. As will be described in more detail below, each of the entity identifier 104, person identifier 105, position identifier 106, and status identifier 108 may output their predictions/identifications along with a confidence value.

The entity identifier 104, person identifier 105, position identifier 106, status identifier 108, and other processing modules described herein may utilize one or more machine-learning technologies. Non-limiting examples of such machine-learning technologies can include Feedforward Networks, Recurrent Neural Networks (RNN), Long short-term Memory (LSTM), Convolutional neural networks, Support-vector machines (SVM), and Decision Trees. The various identifiers, engines, and other processing blocks described herein may be trained via supervised and/or unsupervised learning utilizing these, or any other appropriate, machine learning technologies to make the described assessments, decisions, identifications, etc. It should be understood, however, that this description is not intended to put forth new technologies for making such assessments, decisions, identifications, etc. Instead, this description is intended to manage computational resources, and as such, is meant to be compatible with any type of processing module.

The entity identifier 104 may output an entity identity 112 of a detected entity, and such entity identity may have any suitable degree of specificity. In other words, based on received sensor data, the entity tracker 100 may predict the identity of a given entity, and output such information as entity identity 112. For example, the entity identifier 104 may report that a particular entity is a piece of furniture, a dog, a human male, etc. Additionally, or alternatively, the entity identifier 104 may report that a particular entity is an oven with a particular model number; a pet dog with a specific name and breed; an owner or known user of smart assistant computer 20, with the owner/known user having a particular name and profile; etc. In some examples, the degree of specificity with which the entity identifier 104 identifies/classifies detected entities may depend on one or more of user preferences and sensor limitations.

When applied to people, the entity tracker 100 may in some cases collect information about individuals whom it is unable to identify by name. For example, the entity identifier 104 may record images of a person's face, and associate these images with recorded audio of the person's voice. Should the person subsequently speak to or otherwise address the smart assistant computer 20, the entity tracker 100 will then have at least some information regarding with whom the smart assistant computer is interacting. In some examples, the smart assistant computer 20 could also prompt the person to state their name, so as to more easily identify the person in the future.

In some examples, the smart assistant computer 20 may utilize a person's identity to customize a user interface for the person. In one example, a user may be identified who has limited visual capabilities. In this example and based on this identification, a display of the smart assistant computer 20 (or other device with which the user is interacting) may be modified to display larger text, or to provide a voice-only interface.

The position identifier 106 may be configured to output an entity position (i.e., location) 114 of a detected entity. In other words, the position identifier 106 may predict the current position of a given entity based on collected sensor data, and output such information as entity position 114. As with the entity identity 112, the entity position 114 may have any suitable level of detail, and this level of detail may vary with user preferences and/or sensor limitations. For example, the position identifier 106 may report that a detected entity has a two-dimensional position defined on a plane such as a floor or wall. Additionally, or alternatively, the reported entity position 114 may comprise a three-dimensional position of a detected entity within a real world, three-dimensional environment. In some examples an entity position 114 may comprise a GPS position, a location within a mapping coordinate system, etc.

The reported entity position 114 for a detected entity may correspond to the entity's geometric center, a particular part of the entity that is classified as being important (e.g., the head of a human), a series of boundaries defining the borders of the entity in three-dimensional space, etc. The position identifier 106 may further calculate one or more additional parameters describing the position and/or orientation of a detected entity, such as a pitch, roll, and/or yaw parameter. In other words, the reported position of a detected entity may have any number of degrees-of-freedom, and may include any number of coordinates defining the position of the entity in an environment. In some examples, an entity position 114 of a detected entity may be reported even if the entity tracker 100 is unable to identify the entity, and/or determine the current status of the entity.

Status identifier 108 may be configured to output an entity status 116 of a detected entity. In other words, the entity tracker 100 may be configured to predict the current status of a given entity based on received sensor data, and output such information as entity status 116. "Entity status" can refer to virtually any measurable or classifiable property, activity, or behavior of a given entity. For example, when applied to a person, the entity status of the person can indicate a posture of the person (e.g., standing, sitting, laying down), a speed at which the person is walking/running, a current activity of the person (e.g., sleeping, watching TV, working, playing a game, swimming, talking on the phone), a current mood of the person (e.g., by evaluating the person's facial expression or tone of voice), biological/physiological parameters of the person (e.g., the person's heart rate, respiration rate, oxygen saturation, body temperature, neurological activity), whether the person has any current or upcoming calendar events/appointments, etc. "Entity status" can refer to additional/alternative properties or behaviors when applied to other creatures or non-living objects, such as a current temperature of an oven or kitchen sink, whether a device (e.g., television, lamp, microwave) is powered on, whether a door is open, etc.

In some examples, the status identifier 108 may use sensor data to calculate a variety of different biological/physiological parameters of a human. This may be done in a variety of suitable ways. For example, the entity tracker 100 may be configured to interface with an optical heart rate sensor, a pulse oximeter, a sphygmomanometer, electrocardiograph, etc. Additionally or alternatively, the status identifier 108 may be configured to interpret data from one or more cameras and/or other sensors in an environment, and process the data in order to calculate a human's heart rate, respiration rate, oxygen saturation, etc. For example, the status identifier 108 may be configured to utilize Eulerian magnification and/or similar techniques to amplify miniscule movements or changes captured by the cameras, thereby allowing the status identifier to visualize the flow of blood through a human's circulatory system and calculate associated physiological parameters. Such information can be used, for example, to determine when the person is asleep, working out, in distress, experiencing health problems, etc.

Upon determining one or more of the entity identity 112, entity position 114, and entity status 116, such information may be sent as context information 110 to any of a variety of external modules or devices, where it may be used in a variety of ways. For example, context information 110 may be used by commitment engine 60 to manage commitments and associated messages and notifications. In some examples, context information 110 may be used by commitment engine 60 to determine whether a particular message, notification, or commitment should be executed and/or presented to a user. Similarly, context information 110 may be utilized by voice listener 30 when interpreting human speech or activating functions in response to a keyword trigger.

As noted above, in some examples the entity tracker 100 may be implemented in a single computing device. In other examples, one or more functions of the entity tracker 100 may be distributed across multiple computing devices working cooperatively. For example, one or more of the entity identifier 104, person identifier 105, position identifier 106, and status identifier 108 may be implemented on different computing devices, while still collectively comprising an entity tracker configured to perform the functions described herein. As indicated above, any or all of the functions of the entity tracker may be performed by individual sensors 102. Further, in some examples entity tracker 100 may omit one or more of the entity identifier 104, person identifier 105, position identifier 106, and status identifier 108, and/or include one or more additional components not described herein, while still providing context information 110. Additional details regarding components and computing aspects that may be used to implement entity tracker 100 are described in more detail below with respect to FIG. 12.

Each of entity identity 112, entity position 114, and entity status 116 may take any suitable form. For example, each of the entity identity 112, position 114, and status 116 may take the form of a discrete data packet including a series of values and/or labels describing the information gathered by the entity tracker. Each of the entity identity 112, position 114, and status 116 may additionally include a confidence value defining a statistical likelihood that the information is accurate. For example, if the entity identifier 104 receives sensor data that strongly indicates that a particular entity is a human male named "John Smith," then entity identity 112 may include this information along with a corresponding relatively high confidence value, such as 90% confidence. If the sensor data is more ambiguous, then the confidence value included in entity identity 112 correspondingly may be relatively lower, such as 62%. In some examples, separate predictions may be assigned separate confidence values. For example, the entity identity 112 may indicate with 95% confidence that a particular entity is a human male, and indicate with a 70% confidence that the entity is John Smith. Such confidence values (or probabilities) may be utilized by a cost function in generating cost calculations for providing messages or other notifications to a user and/or performing action(s).

In some implementations, the entity tracker 100 may be configured to combine or fuse data from multiple sensors in order to output more accurate predictions. As an example, a camera may locate a person in a particular room. Based on the camera data, the entity tracker 100 may identify the person with a confidence value of 70%. However, the entity tracker 100 may additionally receive recorded speech from a microphone. Based on the recorded speech alone, the entity tracker 100 may identify the person with a 60% confidence value. By combining the data from the camera with the data from the microphone, the entity tracker 100 may identify the person with a higher confidence value than would be possible using the data from either sensor alone. For example, the entity tracker may determine that the recorded speech received from the microphone corresponds to lip movements of the person visible to the camera when the speech was received, and thereby conclude with relatively high confidence, such as 92%, that the person visible to the camera is the person speaking. In this manner, the entity tracker 100 may combine the confidence values of two or more predictions to identify a person with a combined, higher confidence value.

In some examples, data received from various sensors may be weighted differently depending upon a reliability of the sensor data. This can be especially relevant in situations where multiple sensors are outputting seemingly inconsistent data. In some examples, the reliability of a sensor's data may be based at least in part on the type of data generated by the sensor. For example, in some implementations a reliability of video data may be weighted higher than a reliability of audio data, as the presence of an entity on camera may be a better indicator of its identity, position, and/or status than recorded sounds that are presumed to originate from the entity. It will be appreciated that a reliability of sensor data is a different factor than a confidence value associated with a predicted accuracy of an instance of data. For example, several instances of video data may have different confidence values based on different contextual factors present at each instance. Each of these instances of video data, however, may be associated with a single reliability value for video data in general.

In one example, data from a camera may suggest that a particular person is in a kitchen with a 70% confidence value, such as via face recognition analysis. Data from a microphone may suggest with a 75% confidence value that the same person is in a nearby hallway, such as via voice recognition analysis. Even though the instance of microphone data carries a higher confidence value, the entity tracker 100 may output a prediction that the person is in the kitchen based on a higher reliability of the camera data as compared to a lower reliability of the microphone data. In this manner and in some examples, different reliability values for different sensor data may be used along with confidence values to reconcile conflicting sensor data and determine an identity, position, and/or status of an entity.

Additionally, or alternatively, more weight may be given to sensors that have higher precision, more processing power or otherwise greater capabilities. For example, a professional-grade video camera may have a significantly improved lens, image sensor, and digital image processing capabilities as compared to a basic webcam found in a laptop. Accordingly, a higher weight/reliability value may be given to video data received from the professional-grade camera as compared to the webcam, as such data is likely to be more accurate.

Figure 4:
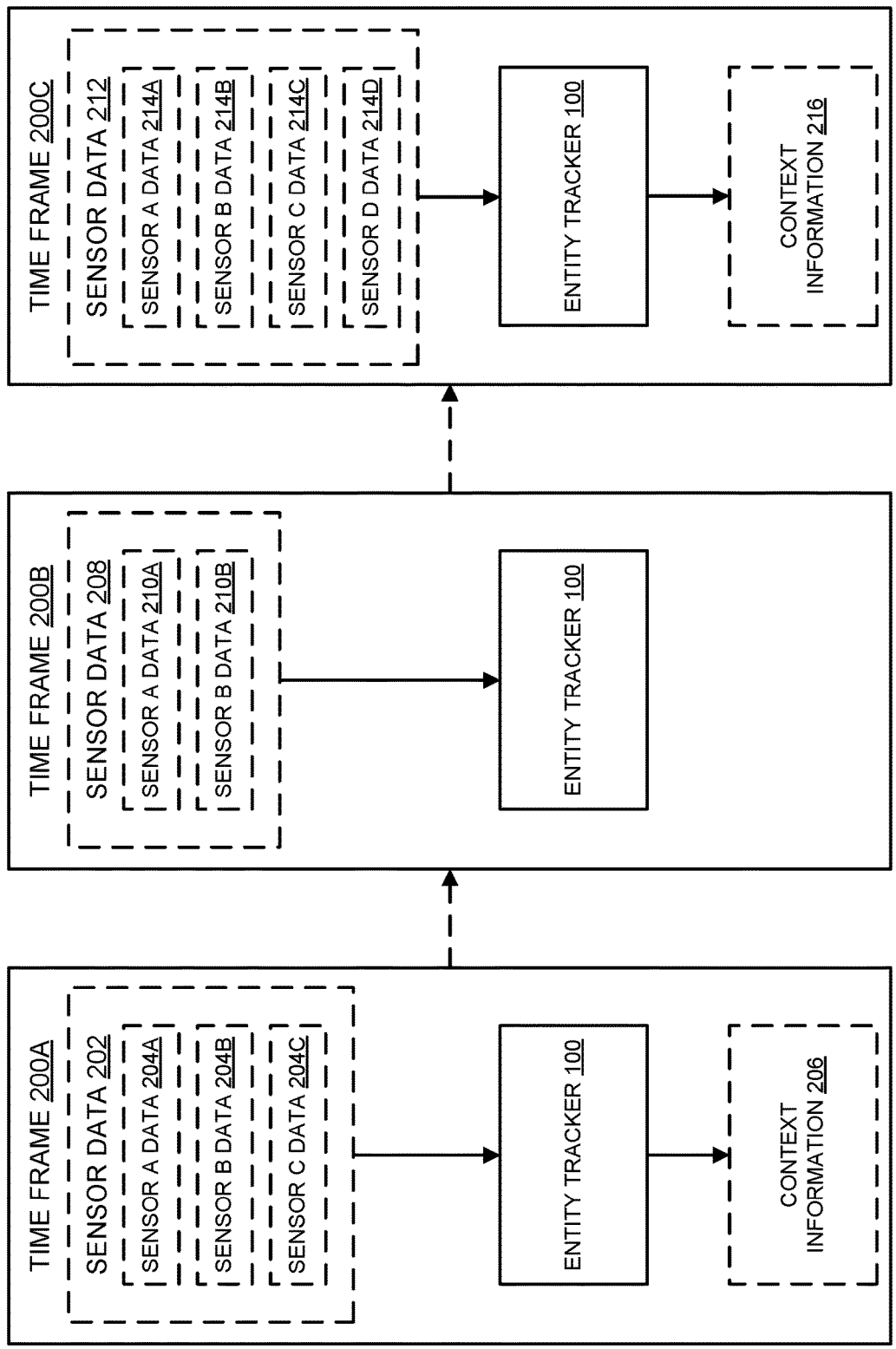
FIG. 4 schematically shows an entity tracker receiving and interpreting sensor data over multiple time frames according to examples of the present disclosure.

With reference now to FIG. 4, in some examples, individual sensors used with the entity tracker 100 may output data with a different frequency than other sensors used with the entity tracker. Similarly, sensors used with the entity tracker 100 may output data with a different frequency than the frequency with which the entity tracker evaluates the data and outputs context information. In the example of FIG. 4, entity tracker 100 may receive and interpret sensor data over multiple time frames 200A, 200B, and 200C. A single time frame may represent any suitable length of time, such as $\frac{1}{30}^{th}$ sec., $\frac{1}{60}^{th}$ sec., etc.

In this example, during time frame 200A entity tracker 100 receives a set of sensor data 202 including sensor A data 204A, sensor B data 204B, and sensor C data 204C. Such sensor data is interpreted by entity tracker 100 and transformed into context information 206, which may be used to determine an identity, position, and/or status of one or more detected entities as described above. During time frame 200B, entity tracker 100 receives sensor data 208, including sensor A data 210A and sensor B data 210B. Entity tracker 100 does not receive data from sensor C during time frame 200B, as sensor C outputs data at a different frequency than sensors A and B. Similarly, entity tracker 100 does not output context information during time frame 200B, as the entity tracker outputs context information at a different frequency than sensors A and B.

During time frame 200C, entity tracker 100 receives sensor data 212, including sensor A data 214A, sensor B data 214B, sensor C data 214C, and sensor D data 214D. Entity tracker 100 also outputs context information 216 during time frame 200C, which may be based on any or all of the sensor data received by the entity tracker since context information was last output in time frame 200A. In other words, context information 216 may be based at least in part on sensor data 208 as well as sensor data 212. In some examples, context information 216 may be based at least in part on sensor data 202 and sensor data 208, as well as sensor data 212.

As shown in FIG. 4, after the entity tracker 100 receives data from a particular sensor, multiple time frames may pass before the entity tracker receives more data from the same sensor. During these multiple time frames, entity tracker 100 may output context information. Similarly, the usefulness of data received from a particular sensor may vary from time frame to time frame. For example, at a first time frame the entity tracker 100 may receive audio data of a particular person speaking via a microphone, and accordingly identify an entity position 114 of the person with a relatively high confidence value. In subsequent time frames, the person may remain at the identified position, but also may have stopped speaking since the first time frame. In this case, the absence of useful data from the microphone may not be a reliable indicator of the absence of the person. Similar issues can arise with other types of sensors. For example, a camera may lose track of a person if he covers his face, or is occluded by an obstacle, such as another person or a moving object. In this case, though current camera data may not suggest the presence of the person, prior instances of camera data may suggest that the person is still located at the previously identified position. In general, while sensor data may reliably indicate the presence of an entity, such data may be less reliable in suggesting the absence of an entity.

Accordingly, the entity tracker 100 may utilize one or more confidence decay functions, which in different examples may be defined by the entity tracker and/or by the sensors themselves. A confidence decay function may be applied to sensor data to reduce the entity tracker's confidence in the data from a particular sensor as time passes since that sensor last positively detected an entity. As an example, after a sensor detects an entity at a particular location, the entity tracker 100 may report context information 110 indicating that the entity is at the location with relatively high confidence. If after one or more time frames the sensor no longer detects the entity at the location, and unless it subsequently gathers contradictory evidence, the entity tracker 100 still may report that the entity is at the location, though with a somewhat lower confidence. As time continues to pass since the sensor last detected the entity at the location, it becomes progressively less likely that the entity is still at the location. Accordingly, the entity tracker 100 may utilize the confidence decay function to progressively decrease the confidence value of its reported context information 110, eventually reaching 0% confidence if no additional sensors detect the entity.

In some cases, different confidence decay functions may be utilized with different sensors and sensor types. A selection of a particular decay function may depend at least in part on particular properties of a sensor. For example, confidence values associated with data from a video camera may decay more rapidly than confidence values associated with data from a microphone, as absence of an entity in a video frame is a more reliable indicator of the entity's absence than silence recorded by a microphone.

Figure 5:
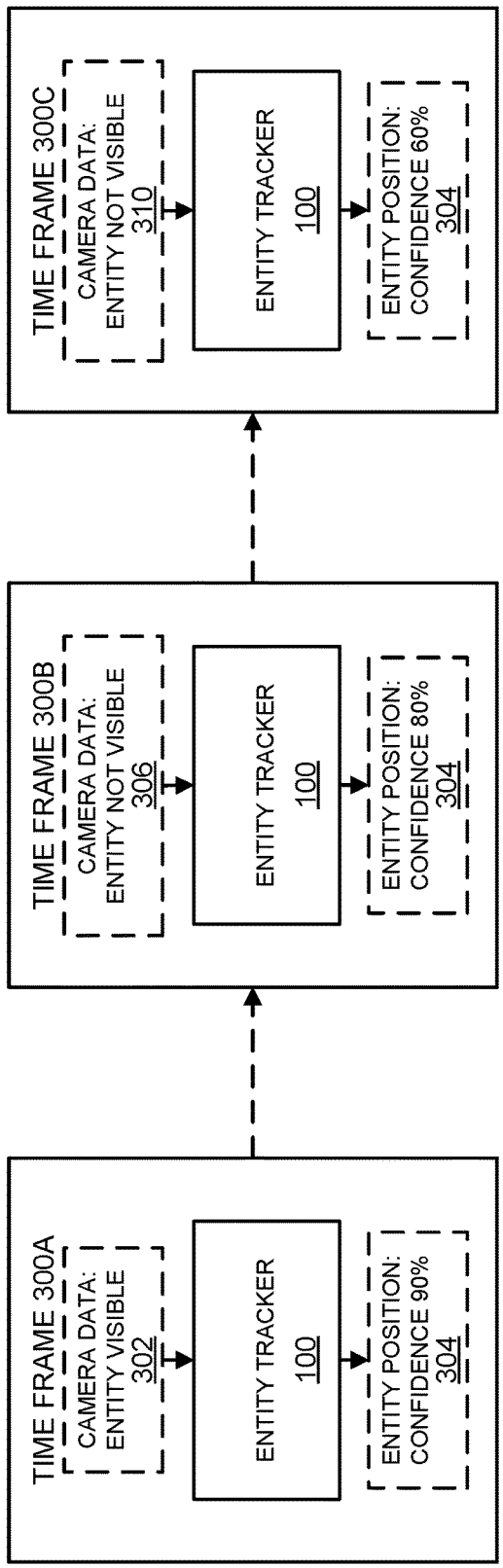
FIG. 5 schematically shows an example of sensor confidence decay over time via an entity tracker according to an example of the present disclosure.

One example of sensor confidence decay is schematically illustrated in FIG. 5, which shows entity tracker 100 receiving sensor data during three different time frames 300A, 300B, and 300C. During time frame 300A, entity tracker 100 receives camera data 302 in which an entity is visible in the frame. Based on this data, the entity tracker 100 reports the entity position 304 with a 90% confidence value. In time frame 300B, entity tracker 100 receives camera data 306 in which the entity is no longer visible in the frame. However, it is possible that the entity has not moved, and has merely become occluded, or otherwise undetectable to the camera. Accordingly, entity tracker 100 reports the same entity position 304, but with a lower confidence value of 80%.

Finally, in time frame 300C entity tracker 100 receives camera data 310 indicating that the entity is still not visible in the frame. As time has passed, it has grown less likely that the entity is still in the same position. Accordingly, the entity tracker 100 reports the same entity position 304 with a still lower confidence value of 60%.

In some examples, variable reliability of sensor data may be at least partially addressed by making use of data filtering techniques. In some examples, a Kalman filter may be utilized to filter sensor data. A Kalman filter is a mathematical function that may combine multiple uncertain measurements and output a prediction with more confidence than would be possible using any individual measurement. Each measurement input to the Kalman filter is given a weight based on the measurement's perceived reliability. Kalman filters operate in a two-step process, including a prediction step and an update step. During the prediction step, the filter outputs a prediction based on recent weighted measurements. During the update step, the filter compares its prediction to an actual observed value or state, and dynamically adjusts the weighting applied to each measurement so as to output more accurate predictions.

In some examples, entity tracker 100 may comprise a Kalman filter that combines data from a variety of sensors to compensate for lower sensor reliability, such as when sensor confidence values have decayed over time since the last positive detection. In some examples, entity tracker 100 may apply a Kalman filter to sensor data when one or more sensor confidence values are below a predetermined threshold. In an example scenario, image data from a camera may be analyzed using face detection techniques to reliably detect a person in a particular room. In response, the entity tracker 100 may report with high confidence that the person is located in the room.

In subsequent time frames, the camera may no longer be able to capture and/or positively recognize the person's face in the room. For example, the person's face may become occluded, or the camera may transmit data with a much lower frequency than the entity tracker 100 outputs context information 110. If the entity tracker 100 relied exclusively on data from the camera, then the confidence value of its reported position of the person would gradually decrease until the next positive detection. However and in some examples, data from the camera may be supplemented with data from other sensors. For example, during the subsequent time frames a microphone may report that it hears the person's voice in the room, or another sensor may report that it can detect the presence of the person's portable computing device in the room. In such cases, this data may be assigned weights by the Kalman filter, and may be used to predict the person's current location with more confidence than would be possible if only the camera data were used.

In some cases, detection of people and/or other entities in an environment can become more complicated when sensor data is contaminated by background information. Such background information may compromise the confidence with which the entity tracker 100 reports entity identity 112, position 114, and/or status 116. For example, the smart assistant computer 20 may need to determine the identity of a person who is speaking in order to appropriately respond to a query or command. Such a determination can be difficult when multiple people are speaking at the same time, a television is playing, loud machinery is operating, etc.

Accordingly, the entity tracker 100 may use a variety of audio processing techniques to more confidently identify a particular active participant who is engaged in a conversation with other people and/or with the smart assistant computer 20. As an example, the entity tracker 100 may implement a voice activity detection (VAD) engine that may distinguish human voices from environmental noise, and identify the presence or absence of human speech.

General-purpose VAD engines may be used for the purpose of classifying a particular segment of audio as including either speech or non-speech, with a corresponding confidence value. An entity tracker 100 also may utilize a speaker recognition engine to match a particular audio segment with a particular person. As more speech is received, the speaker recognition engine may be progressively tailored to classify the audio as including speech from a particular conversation participant, or not including speech from the particular conversation participant. In this manner, the entity tracker 100 may recognize speech from one or more particular persons/conversation participants.

Training of a speaker recognition engine may occur any time the entity tracker 100 has confidently identified a particular person and recorded audio that can be confidently attributed to that person. For example, using camera data, the entity tracker 100 may identify a particular person and determine that the person's lips are moving. The entity tracker 100 may simultaneously receive audio from a microphone that can be safely assumed to include speech from the identified person. Accordingly, the received audio can be used to retrain the speaker recognition engine to more specifically recognize the identified person's voice.

In some cases, such retraining may occur only when the person has been identified with a high confidence value (e.g., via accurate facial recognition or any other method), such as a confidence value exceeding a predetermined threshold, and when the entity tracker 100 has received an audio recording of the person's voice having high volume/amplitude and a high signal-to-noise ratio (S/N). Using this technique, the entity tracker 100 may accumulate a variety of person-specific voice models, allowing the entity tracker to more consistently identify speech from particular people and ignore background noise.

Figure 6:
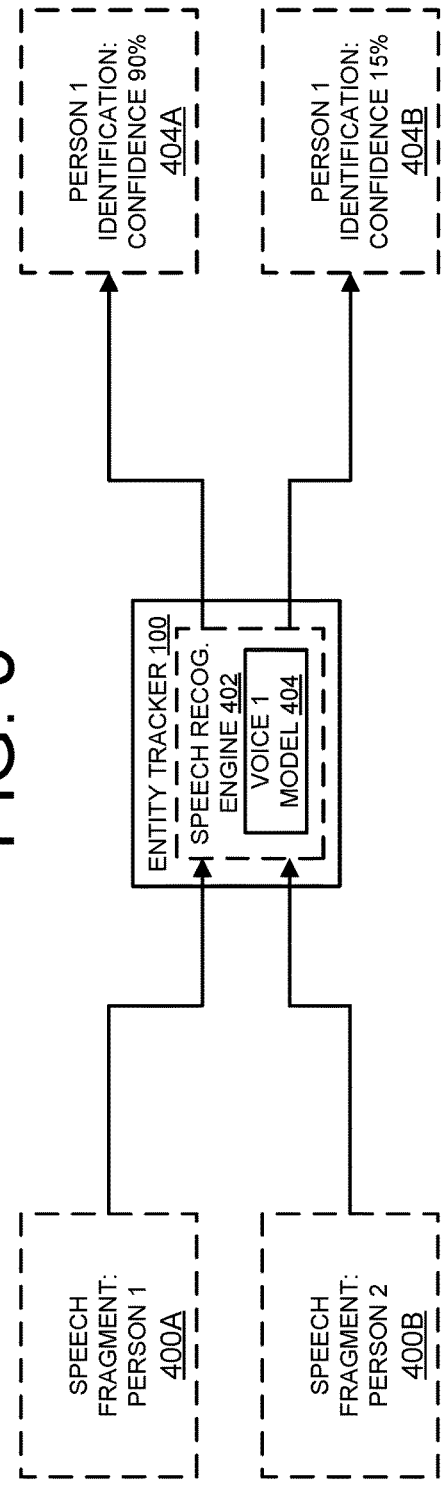
FIG. 6 schematically shows an example of using a trained voice recognition engine to recognize a person's speech according to examples of the present disclosure.

With reference now to FIG. 6, an example of using a trained speech recognition engine to recognize speech from a particular person is schematically illustrated. In this example, entity tracker 100 receives two speech fragments 400A and 400B. Speech fragment 400A includes recorded speech of a person 1, and speech fragment 400B includes recorded speech of a person 2. Entity tracker 100 includes a speech recognition engine 402 that has been specifically trained to recognize speech from person 1 using a voice 1 model 404, as described above. Voice 1 model 404 may be applied to each of speech fragment 400A and speech fragment 400B as they are received by the entity tracker 100.

Upon processing the speech fragments, the entity tracker 100 outputs a prediction of the likelihood that each speech fragment corresponds to person 1. As shown, for speech fragment 400A, the entity tracker outputs a person 1 identification 404A with a 90% confidence value, indicating that the speech fragment likely includes speech from person 1. For speech fragment 400B, the entity tracker outputs a person 1 identification 404B with a 15% confidence value, indicating that speech fragment 400B likely does not include speech from person 1.

In some examples, an entity tracker 100 may be configured to identify background noise present in an environment, and use audio processing techniques to subtract such background noise from received audio data. For example, a particular device in a person's home may be playing background audio, such as music or television/movie dialogue. Various microphone-equipped devices in the person's home may record such audio. Where such microphone-equipped devices include the smart assistant computer 20 and/or provide audio data to the entity tracker 100, such background audio may compromise the ability of the system to identify, interpret and/or respond to human questions or commands.

Accordingly and in some examples, the device playing the background audio and/or another microphone-equipped device recording the background audio may send the captured audio signal to the entity tracker 100. In this manner, the entity tracker 100 may subtract the background audio from the audio signal received from the microphone-equipped devices. In some examples, the subtraction of the background audio signal from the recorded audio data may be performed by the device(s) that capture the audio data, or by associated audio-processing components, prior to sending the audio data to the entity tracker 100.

Additionally or alternatively, devices and/or the entity tracker 100 may be trained to recognize particular sources of background noise (e.g., from an air vent or refrigerator), and automatically ignore waveforms corresponding to such noise in recorded audio. In some examples, an entity tracker 100 may include one or more audio-recognition models trained specifically to recognize background noise. For example, audio from various noise databases may be run through unsupervised learning algorithms in order to more consistently recognize such noise. By allowing the entity tracker 100 to recognize irrelevant background noise, the ability of the entity tracker to recognize relevant human speech and other sounds may be improved. In some implementations, positional knowledge of a sound source may be used to focus listening from a directional microphone array.

In some examples, and depending on the sensors and processing methods used by the entity tracker 100, tracking and identification of entities in an environment can be time-consuming and resource-intensive. For example, machine learning facial recognition algorithms may be computationally expensive. Accordingly, the entity tracker 100 may use a variety of techniques to selectively choose when resource-intensive processing should be utilized. In this manner, the efficiency of the entity tracker 100 may be improved without compromising its corresponding functionality.

Figure 7:
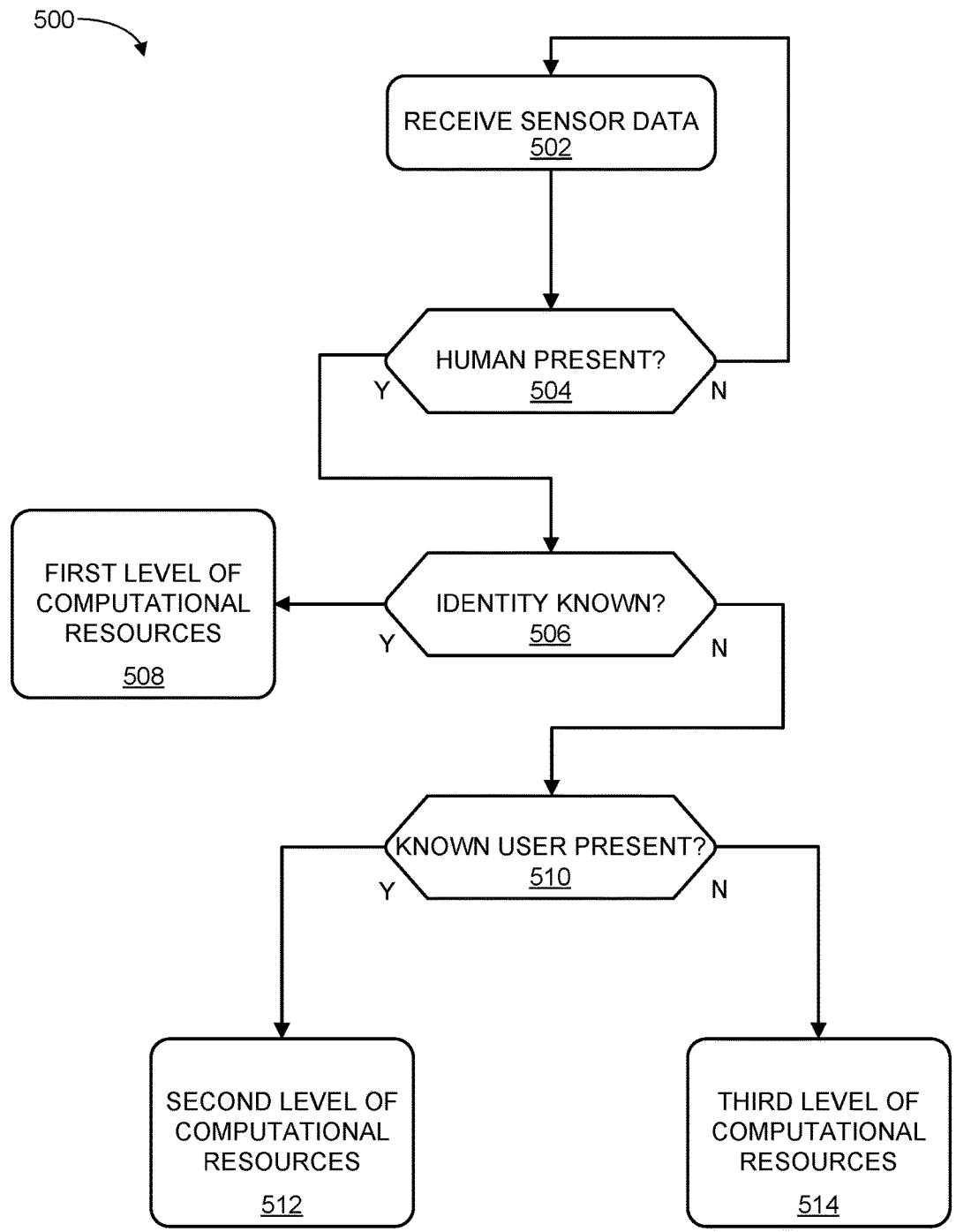
FIG. 7 illustrates a flowchart for identifying humans in a physical environment.

To illustrate this, FIG. 7 shows an example flowchart for a computationally-efficient method 500 for identifying humans (e.g., human 2 of FIG. 1) in a physical environment (e.g., living room 4 of FIG. 1). In some examples, some or all of the steps of method 500 may be performed by entity tracker 100 described above. However, it will be understood that the computer resource conservation techniques described herein need not be restricted to any particular technology for tracking or identifying humans. Rather, the techniques described herein relate to when such tracking and identification technologies should or should not be applied, with the aim of conserving computer resources.

At 502, method 500 includes receiving data from one or more sensors configured to monitor a physical environment. Such sensors may, for instance, take the form of sensors 102 of FIG. 3, camera 12 of FIG. 1, and/or any other suitable sensors.

At 504, method 500 includes computer-analyzing the sensor data to recognize presence of a human in the physical environment. In some cases, as described above, the sensor data may be received by entity tracker 100 and computer-analyzed by the entity tracker to output context information 110. Should it be determined that a human is present in the physical environment, method 500 proceeds to 506. In contrast, if it is determined that there is no human present in the physical environment, method 500 returns to 502, and continues monitoring sensor data of the physical environment.

In some examples, computer-recognizing the received sensor data to recognize presence of a human can include detecting motion in the physical environment corresponding to human movement. Motion in a physical environment can be detected in any of a variety of suitable ways. As a non-limiting example, motion can be detected via identifying a change in a feed from a camera, such as a visible-light or infrared (IR) camera (e.g., a new shape appears in a visible-light feed, or a new IR signature appears on the IR feed). Upon detecting motion in the physical environment, the smart assistant computer can utilize additional computational resources to confirm that the detected motion corresponds to presence of a human. For example, processing can be done on visible-light and/or IR feeds to attempt to recognize a human silhouette.

In some examples, and with the aim of conserving computational resources, the smart assistant computer may severely limit or altogether refrain from performing motion detection until after some other indication of human presence is received. In other words, when there is no indication of human presence, the smart assistant computer may dedicate a baseline or minimum level of computational resources to tracking entities in the physical environment. This can both save electrical power, as less is consumed by processors and sensors of the smart assistant device, as well as computer processing power, which can instead be allocated to other tasks. Once the smart assistant computer receives some indication that a human or other entity is present in the physical environment, the smart assistant computer can allocate additional resources as needed. As an example, the smart assistant computer may receive an indication (e.g., via a "smart home" sensor) that an entrance door of the physical environment has opened. This can serve as an initial indicator that a human has entered the physical environment, and justify expending additional computing resources on motion detection to recognize presence of the human.

It will be understood that motion detection can also begin in response to other indications of potential human presence. As non-limiting examples, such indications can include detecting that one or more light sources in the physical environment have been activated, detecting that a new portable electronic device has entered the physical environment (e.g., by receiving a connection or pairing request from the device), and/or other suitable indicators.

In addition to, or as an alternative to detecting motion, the smart assistant computer can recognize presence of a human in the physical environment in other suitable ways, as described above with respect to entity tracker 100. Other non-limiting indicators of human presence can include recognizing a human shape (e.g., a face or silhouette) in a camera feed, detecting a human voice via a microphone, detecting presence of a portable computing device in a physical environment, receiving an indication that a human is interacting with objects or devices in the physical environment (e.g., opening doors or turning on appliances), determining via a digital calendar that one or more humans are scheduled to be present in the physical environment, etc.

Further, it will be understood that, as described above, the smart assistant computer can take any or all of the potential indicators of human presence into account when evaluating human presence in the physical environment. In other words, recognizing human presence can include predicting, with a certain confidence value, human presence in the environment based on a plurality of different indicators and sensor values, each having their own associated confidence values and reliability factors. If there is little evidence to support the prediction that a human is present in the physical environment, the confidence value may be relatively low, such as 15%. In contrast, if numerous relatively reliable sensors each indicate that a human is likely present in the environment, then the confidence value may be relatively high, such as 90%. In some examples, the smart assistant computer may recognize human presence in the physical environment any time the confidence value exceeds a threshold such as, for example, 70%.

At 506 of method 500, once human presence in the physical environment is recognized, the smart assistant computer attempts to identify the human. Once again, this may be done in any of a variety of suitable ways, as described above with respect to the entity identification techniques used by entity tracker 100. Notably, this initial identification attempt may be done using identification techniques that require relatively few computational resources. As examples, such techniques can include relatively "coarse" facial recognition algorithms, applying facial recognition algorithms to relatively low-resolution down-sampled images, using voice recognition algorithms that rely on relatively low-resolution audio samples, identifying the human based on their body shape, hair/skin color, etc.

Upon confirming the identity of the human, method 500 proceeds to 508, at which the smart assistant computer dedicates a first level of computational resources to track the human. As indicated above, the computational resources expended by the smart assistant computer at any given time can be scaled up or down as needed. Prior to receiving an indication that a human is present in the environment, the smart assistant computer may dedicate a baseline or minimal level of computational resources to monitoring the physical environment. Upon receiving an indication that a human is present in the environment, the smart assistant computer can allocate additional computational resources to confirm human presence and attempt to identify the human. Once this is done, however, the smart assistant computer may reduce its resource expenditure to a first level of computational resources which can include, for example, operating one or more sensors of the smart assistant computer at a reduced sampling frequency. Other suitable methods of reducing resource expenditure can include, for example, disabling one or more sensors, switching to use less computationally expensive algorithms, deprioritizing processing threads associated with entity identification and tracking, etc.

In some implementations, a smart assistant computer as described herein can provide various security features in conjunction with entity tracking and identification. For example, upon initially failing to identify a human in a physical environment, the smart assistant computer can scale up its use of computational resources during subsequent attempts to identify the human. The extent to which the smart assistant computer's resource expenditures are increased can depend on a variety of security considerations, and/or various other factors. For example, if the smart assistant computer fails to recognize a human in a physical environment, though a different human in the environment is successfully identified as a known user of the smart assistant computer, then it may not be particularly important that the computer identify the unidentified human, as they are likely someone that the known user knows and trusts. In contrast, if the smart assistant computer fails to recognize a human in the environment while no known users are present, or one or more protected users (e.g., small children) are present, then it may be more important that the smart assistant computer identify the unidentified human.

Accordingly, at 510 of method 500, upon failing to identify the human present in the physical environment, the smart assistant computer determines whether a known user is present in the physical environment. The term "known user" can have any suitable meaning depending on the implementation. For example, "known user" can refer to an owner of the smart assistant computer, an administrator of the smart assistant computer, an owner of the building or area in which the physical environment is located, any registered user of the smart assistant computer, any humans that are regularly detected by the smart assistant computer (e.g., that live in the physical environment), etc. In some examples, ordinary humans can be "promoted" to known users of the smart assistant computer by creating a profile or account on the smart assistant computer, by receiving an invitation or authorization from another known user, via repeated detection by the smart assistant computer, and/or through other suitable ways.

Presence of a known user in the physical environment may be confirmed in any of a variety of suitable ways, for example including any of the entity identification and tracking techniques described above with respect to entity tracker 100. In addition to or as an alternative to the techniques described above, in some cases, presence or absence of the known user can be confirmed by sending a location query to an electronic device associated with the known user. For example, the smart assistant computer may query a smartphone of the known user for its current location. In another example, the smart assistant computer may send a notification to any or all devices associated with the known user, so that such devices can request the known user to confirm their location.

At 512, upon failing to confirm the identity of the human while a known user is present, method 500 includes dedicating a second level of computational resources of the smart assistant computer, greater than the first level of computational resources, to determine the identity of the human. This may include, for example, operating one or more sensors of the smart assistant computer with an increased sampling frequency, relative to the first level of computational resources. However, because the known user is present, the smart assistant computer may continue to limit its expenditure of computational resources, so as not to unnecessarily expend resources attempting to identify an individual that is trusted by the known user. Accordingly, the smart assistant computer may continue to use human identification techniques that are relatively less computationally expensive than techniques that the smart assistant computer may have access to.

Figure 8:
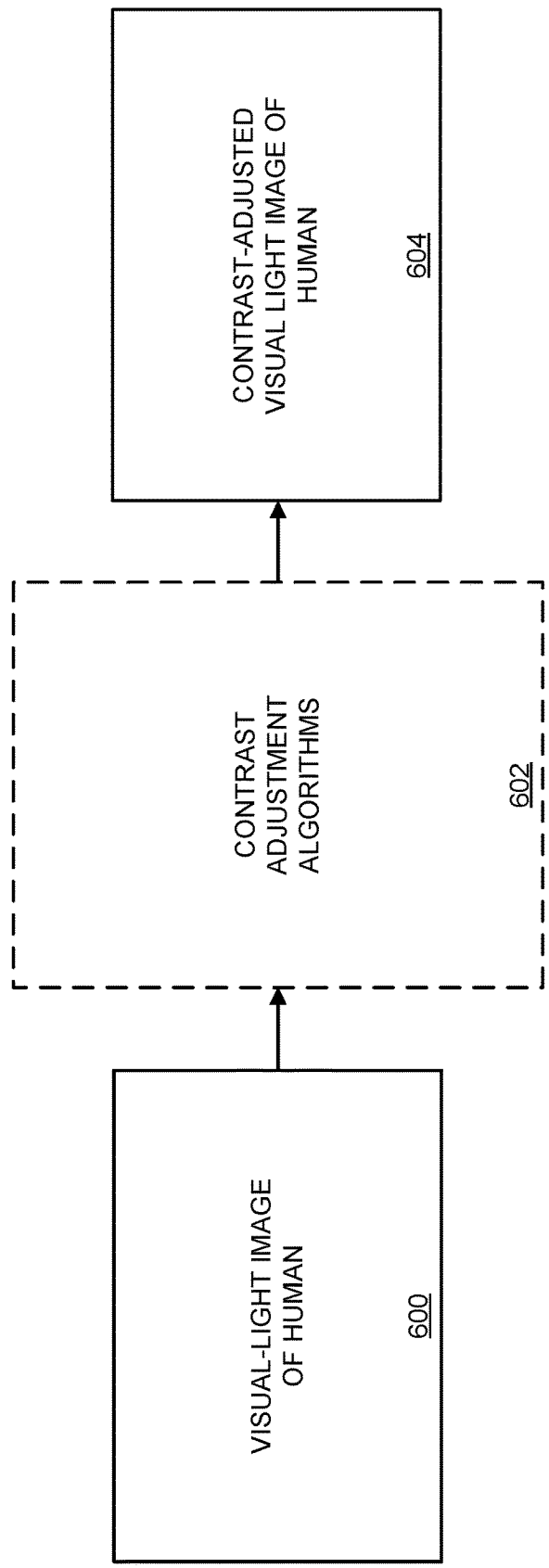
FIG. 8 schematically illustrates contrast adjustment of a visual-light image of a human.

As an example, dedicating the second level of computational resources to determine the identity of the human may include applying a first set of image processing algorithms to a visible-light image of the human captured by a visible-light camera of the one or more sensors. However, this first set of image processing algorithms may be relatively less computationally expensive than a second set of image processing algorithms that may, for example, require more processor operations than the first set of image processing algorithms. In some examples, the image processing algorithms may include one or more contrast adjustment algorithms that may be used, for example, to correct for lighting conditions in the physical environment. As an example, referring to FIG. 1, a visible-light image of human 2 may be captured by camera 12. This is schematically illustrated in FIG. 8, which shows a visible-light image 600 captured of a human in a physical environment. In FIG. 8, a variety of contrast adjustment algorithms 602 are applied to the visual-light image to give a contrast-adjusted visual light image 604.

Many contrast adjustment algorithms are designed to, for an image including a plurality of pixels and each pixel having a luminance value defining that pixel's lightness/darkness, identify minimum and maximum luminance values present in the image. These values can then be transformed into contrast-adjusted minimum and maximum luminance values, which often has the effect of "stretching" the existing contrast in the image to cover a wider range.

One example contrast adjustment algorithm is provided below, where $L_i$ and $H_i$ respectively define the lowest and highest luminance values from the original image, and $L_{CA}$ and $H_{CA}$ refer to contrast-adjusted lowest and highest luminance values:

$$L_{CA} = \text{MAX}\left(30, \frac{Li}{2}\right)$$

$$H_{CA} = \text{MIN}\left(220, Hi + \frac{(255 - Hi)}{2}\right)$$

Note that the above contrast adjustment algorithm assumes that pixel luminance values are given as values ranging from 0-255. In other implementations, the above contrast adjustment algorithm may be modified to operate on the basis of pixel luminance values having any suitable format.

In some cases, the smart assistant computer may detect presence of a human in a physical environment when no known user is present. This can potentially represent a security risk, as the unidentified human may represent an unauthorized intruder into the physical environment. As an example, the smart assistant computer may detect a thief or other criminal that has broken into a known user's home. Accordingly, at 514, upon failing to confirm the identity of the human while no known users are present, method 500 includes dedicating a third level of computational resources of the smart assistant computer, greater than the second level of computational resources, to determine the identity of the human.

In some cases, the third level of computational resources may permit use of relatively expensive entity tracking and identification techniques. Computationally expensive processes may be justified when it is determined that identifying a particular human is more important than conserving resources. Such techniques can include, for example, applying relatively expensive facial recognition algorithms to high-resolution images of the detected human's face, analyzing a gait or posture of the detected human, activating additional sensors, increasing a sampling frequency of sensors, increasing a frequency with which any identification technique is applied, applying a second set of image processing algorithms to a visible-light image of the human, the second set of image processing algorithms requiring more processor operations than the first set of image processing algorithms, prioritizing processor threads associated with human identification over processor threads associated with other tasks, etc. In this manner, the smart assistant computer can prioritize identifying the detected human at the expense of performing other tasks that may be deemed less important given the threat of a potential security risk.

In some cases, dedicating the third level of computational resources can include employing one or more user-invasive identification or security verification techniques. For example, the smart assistant computer may dedicate one or more user interface resources to present a security check to the detected human. The security check can include, for example, requiring the detected human to input a password, submit to biometric scanning (e.g., of the human's fingerprint, face, or iris), answer a security question, use a provided communication feature to contact and receive approval from a known user of the smart assistant computer, etc. In some cases, should the detected human ignore or fail the security check, the smart assistant computer may automatically activate an alarm and/or send one or more notifications to known users, third-party security professionals, and/or law enforcement officials that an unidentified human is present.

Another user-invasive identification technique that may be employed with the third level of computational resources can include sending an identification query to an electronic device associated with one or more known users. Such an identification query can, for example, ask the known user to confirm whether they expect a human to be present in the physical environment. In some cases, the identification query can include a picture of the detected human, and/or other identifying information measurable via sensors. In response to the identification query, the known user can provide the smart assistant computer with an identity of the detected human. Additionally, or alternatively, the identification query may allow the known user to use a communication function to speak with the detected human, contact law enforcement, direct the smart assistant computer to contact law enforcement, etc. Such user-invasive identification techniques may be avoided when a first or second level of computational resources are being used.

In some cases, dedicating the third level of computational resources can include increasing network communication to one or more other smart assistant computers, remote services, and/or other computing devices.

In some examples, any or all of the first, second, and third levels of computational resources used to track and/or identify detected humans can be dynamically scaled based on one or more security factors. In other words, based on the one or more security factors, the smart assistant computer may choose to allocate more or less computational resources to identifying a detected human than would normally be used. For example, a current level of computational resources dedicated to identifying a human may be scaled up when the smart assistant computer is in a high security mode. In other words, the smart assistant computer may have multiple different security settings, which may be set automatically and/or manually by a known user of the smart assistant computer. When the smart assistant computer is in a high security mode, it may expend relatively more computational resources attempting to identify detected humans than would be used in a "medium" or "low" security setting.

As another example, a current level of computational resources dedicated to identifying a detected human may be scaled up during a predetermined period. Such a predetermined period can include, for example, times during which owners/known users of the smart assistant computer are asleep (e.g., during nighttime, or when the smart assistant computer observes that the known users are asleep via sensor data), and/or times when owners/known users are typically away from the physical environment (e.g., at work or on vacation). In some situations, the level of resources used to identify a detected human can be scaled down during other predetermined periods such as, for example, when a known user indicates that a known or trusted visitor will be entering the physical environment.

In some cases, a current level of computational resources dedicated to identifying a detected human may be scaled up when an unaccompanied protected user is present. A "protected human" can include any humans that have been indicated as requiring extra security including, for example, small children, people with disabilities, important officials or celebrities, etc. Such protected users may be designated manually by known users of the smart assistant computer, and/or automatically identified by the smart assistant computer (e.g., all children below a certain age/size are automatically designated as protected users). In an example scenario, the smart assistant computer may detect an unidentified human in the same room with a young child, and dedicate relatively more computational resources to identifying the detected human in case the detected human intends to harm the child.

With reference now to FIGS. 9-11, additional example implementations of smart assistant computer 20 in a single computing device and across multiple computing devices are illustrated. Additional details regarding components and computing aspects of computing devices illustrated in FIGS. 9-11 are described below with reference to FIG. 12.

FIG. 9 shows an example of an all-in-one computing device 160 in which the components implementing smart assistant computer 20 are arranged together in a standalone device. In some examples, all-in-one computing device 160 may be communicatively coupled to one or more other computing devices 162 via a network 166. In some examples, all-in-one computing device 160 may be communicatively coupled to a data store 164 that may store a variety of data, such as user profile data. All-in-one computing device 160 includes at least one sensor 22, voice listener 30, parser 40, intent handler 50, commitment engine 60, entity tracker 100, and at least one output device 70. Sensor(s) 22 include at least one microphone to receive natural language inputs from a user. In some examples one or more other types of sensor(s) 22 also may be included.

As described above, voice listener 30, parser 40, and intent handler 50 work in concert to convert natural language inputs into commitments that are executable by the all-in-one device 160. The commitment engine 60 stores such commitments in a commitment storage 626. The entity tracker 100 may provide context information to the commitment engine 60 and/or other modules. At a contextually appropriate time, the commitment engine 60 may execute a commitment and provide output, such as audio signals, to output device(s) 70.

FIG. 10 shows an example implementation in which one or more remote services 170 perform the natural language processing functionality of smart assistant computer 20. In this example, voice listener 30, parser 40, intent handler 50, entity tracker 100 and commitment engine 60 reside on one or more computing devices, such as one or more servers, that are remotely located from a cloud-supported user device A. Sensor data from one or more sensors 22 of the user device A is provided to remote service(s) 170 via a network. For example, audio data of a user speaking may be captured by a microphone of user device A and provided to voice listener 30.

As described above, voice listener 30, parser 40, and intent handler 50 cooperate to convert the audio data into commitments that are stored in commitment engine 60. At a contextually appropriate time, the commitment engine 60 may execute a commitment and provide output, such as audio signals, to one or more output device(s) 70 of the user device A.

FIG. 11 shows another example implementation in which one or more remote services 170 perform the natural language processing functionality of smart assistant computer 20. In this example, the one or more remote services 170 are communicatively coupled with a plurality of different sensors 22 and output devices 70. In this example, the sensors include individual standalone sensors A and C, such as microphones, cameras, etc. The output devices include individual standalone output devices B and D, such as loudspeakers.

The one or more remote services 170 are also communicatively coupled to a device E that includes one or more sensors F and an output device G. Device E may take the form of a simple standalone device comprising a microphone, speaker and network connectivity components. In other examples, device E may be a mobile phone, tablet computer, wall-mounted display, or other suitable computing device. In some examples, device E, sensors A and C, and output devices B and D may be part of the same cloud-supported client. In other examples, any number of individual sensors and devices may be utilized with the one or more remote services 170.

As described above, the one or more remote services 170 perform the natural language processing functionality of smart assistant computer 20. In some examples, one or more of the remote services 170 may include all of the natural language processing modules of smart assistant computer 20, as shown in the example of FIG. 10. In other examples, one or more remote services 170 may include less than all of the natural language processing modules, and may be communicatively coupled to the other modules located at one or more other service(s). In the present example, one or more of the remote services 170 also may comprise a device selector 174 that may utilize sensor inputs to select output device B, D and/or G to receive output from the commitment engine 60.

In some embodiments, the methods and processes described herein may be tied to a computing system of one or more computing devices. In particular, such methods and processes may be implemented as a computer-application program or service, an application-programming interface (API), a library, and/or other computer-program product.

Figure 12:
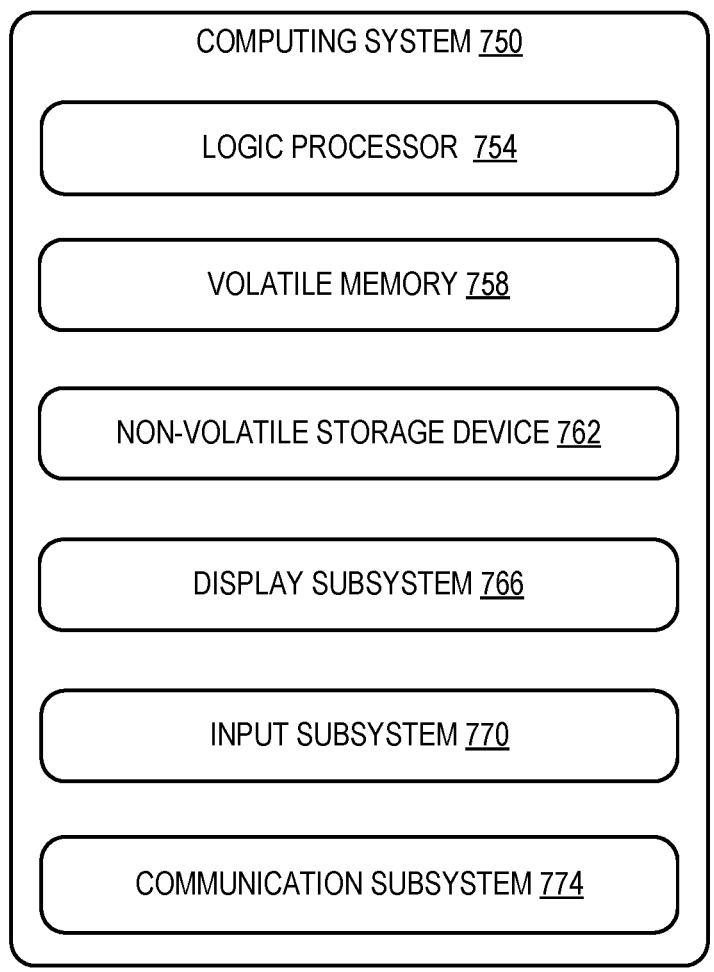
FIG. 12 schematically shows a computing system according to examples of the present disclosure.

FIG. 12 schematically shows a non-limiting embodiment of a computing system 750 that can enact one or more of the methods and processes described above. Computing system 750 is shown in simplified form. Computing system 750 may take the form of one or more smart assistant computers, personal computers, server computers, tablet computers, home-entertainment computers, network computing devices, gaming devices, mobile computing devices, mobile communication devices (e.g., smartphone), and/or other computing devices. As non-limiting examples, any or all of the computing devices described above (e.g., all-in-one computing device 10, sensors 22, voice listener 30, parser 40, intent handler 50, commitment engine 60, output device 70, entity tracker 100, all-in-one computing device 160, remote computing devices 162, and/or remote services 170) may be implemented as computing system 750.

Computing system 750 includes a logic processor 754, volatile memory 758, and a non-volatile storage device 762. Computing system 600 may optionally include a display subsystem 766, input subsystem 770, communication subsystem 774, and/or other components not shown in FIG. 12.

Logic processor 754 includes one or more physical devices configured to execute instructions. For example, the logic processor may be configured to execute instructions that are part of one or more applications, programs, routines, libraries, objects, components, data structures, or other logical constructs. Such instructions may be implemented to perform a task, implement a data type, transform the state of one or more components, achieve a technical effect, or otherwise arrive at a desired result.

The logic processor 754 may include one or more physical processors (hardware) configured to execute software instructions. Additionally or alternatively, the logic processor may include one or more hardware logic circuits or firmware devices configured to execute hardware-implemented logic or firmware instructions. Processors of the logic processor 754 may be single-core or multi-core, and the instructions executed thereon may be configured for sequential, parallel, and/or distributed processing. Individual components of the logic processor optionally may be distributed among two or more separate devices, which may be remotely located and/or configured for coordinated processing. Aspects of the logic processor 754 may be virtualized and executed by remotely accessible, networked computing devices configured in a cloud-computing configuration. In such a case, these virtualized aspects may be run on different physical logic processors of various different machines.

Volatile memory 758 may include physical devices that include random access memory. Volatile memory 758 is typically utilized by logic processor 754 to temporarily store information during processing of software instructions. It will be appreciated that volatile memory 758 typically does not continue to store instructions when power is cut to the volatile memory.

Non-volatile storage device 762 includes one or more physical devices configured to hold instructions executable by the logic processors to implement the methods and processes described herein. When such methods and processes are implemented, the state of non-volatile storage device 762 may be transformed—e.g., to hold different data.

Non-volatile storage device 762 may include physical devices that are removable and/or built-in. Non-volatile storage device 762 may include optical memory (CD, DVD, HD-DVD, Blu-Ray Disc, etc.), semiconductor memory (ROM, EPROM, EEPROM, FLASH memory, etc.), and/or magnetic memory (hard-disk drive, floppy-disk drive, tape drive, MRAM, etc.), or other mass storage device technology. Non-volatile storage device 762 may include nonvolatile, dynamic, static, read/write, read-only, sequential-access, location-addressable, file-addressable, and/or content-addressable devices. It will be appreciated that non-volatile storage device 762 is configured to hold instructions even when power is cut to the non-volatile storage device.

Aspects of logic processor 754, volatile memory 758, and non-volatile storage device 762 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The terms "module", "program" and "engine" may be used to describe an aspect of computing system 750 implemented to perform a particular function. In some cases, a module, program or engine may be instantiated via logic processor 754 executing instructions held by non-volatile storage device 762, using portions of volatile memory 758. It will be understood that different modules, programs or engines may be instantiated from the same application, service, code block, object, library, routine, API, function, etc. Likewise, the same module, program or engine may be instantiated by different applications, services, code blocks, objects, routines, APIs, functions, etc. The terms modules, programs and engines encompass individual or groups of executable files, data files, libraries, drivers, scripts, database records, etc.

It will be appreciated that a "service", as used herein, is an application program that may be executable across multiple user sessions. A service may be available to one or more system components, programs, and/or other services. In some implementations, a service may run on one or more server-computing devices.

When included, display subsystem 766 may be used to present a visual representation of data held by non-volatile storage device 762. As the herein described methods and processes change the data held by the non-volatile storage device, and thus transform the state of the non-volatile storage device, the state of display subsystem 766 may likewise be transformed to visually represent changes in the underlying data. Display subsystem 766 may include one or more display devices utilizing virtually any type of technology. Such display devices may be combined with logic processor 754, volatile memory 758, and/or non-volatile storage device 762 in a shared enclosure, or such display devices may be peripheral display devices.

When included, input subsystem 770 may comprise or interface with one or more user-input devices. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection, gaze detection, and/or intent recognition; electric-field sensing componentry for assessing brain activity; any of the sensors described with respect to the example use cases and environments discussed above; and/or any other suitable sensor.

When included, communication subsystem 774 may be configured to communicatively couple computing system 750 with one or more other computing devices. Communication subsystem 774 may include wired and/or wireless communication devices compatible with one or more different communication protocols. As non-limiting examples, the communication subsystem may be configured for communication via a wireless telephone network, or a wired or wireless local- or wide-area network. In some embodiments, the communication subsystem may allow computing system 750 to send and receive data to and from other devices via a network such as the Internet.

In an example, a method for a smart assistant computer to track a human comprises: receiving data from one or more sensors configured to monitor a physical environment; computer-analyzing the data to recognize presence of a human in the physical environment; and upon confirming an identity of the human, dedicating a first level of computational resources of the smart assistant computer to track the human; or upon failing to confirm the identity of the human while a known user is present, dedicating a second level of computational resources of the smart assistant computer, greater than the first level of computational resources, to determine the identity of the human; or upon failing to confirm the identity of the human while the known user is absent, dedicating a third level of computational resources of the smart assistant computer, greater than the second level of computational resources, to determine the identity of the human. In this example or any other example, dedicating the first level of computational resources to track the human includes operating at least one of the one or more sensors at a reduced sampling frequency. In this example or any other example, dedicating the second level of computational resources to track the human includes operating at least one of the one or more sensors at an increased sampling frequency. In this example or any other example, dedicating the second level of computational resources to determine the identity of the human includes applying a first set of image processing algorithms to one or both of a visible-light image of the human captured by a visible-light camera of the one or more sensors or an infrared image of the human captured by an infrared camera of the one or more sensors. In this example or any other example, the first set of image processing algorithms includes one or more contrast adjustment algorithms. In this example or any other example, a contrast adjustment algorithm of the one or more contrast adjustment algorithms includes identifying lowest and highest pixel luminance values $L_i$ and $H_i$ in an infrared image of the physical environment, such values ranging from 0 to 255, and changing $L_i$ and $H_i$ to contrast-adjusted values $L_{CA}$ and $H_{CA}$, where $L_{CA}$ is given by $$\text{MAX}\left(30, \frac{Li}{2}\right),$$

and $H_{CA}$ is given by $$\text{MIN}\left(220, Hi + \frac{(255 - Hi)}{2}\right).$$

In this example or any other example, dedicating the third level of computational resources to determine the identity of the human includes applying a second set of image processing algorithms to the visible-light image of the human, the second set of image processing algorithms requiring more processor operations than the first set of image processing algorithms. In this example or any other example, dedicating the third level of computational resources to determine the identity of the human includes prioritizing processor threads associated with human identification over processor threads associated with other tasks. In this example or any other example, dedicating the third level of computational resources to determine the identity of the human includes dedicating one or more user interface resources of the smart assistant computer to satisfy a security check. In this example or any other example, dedicating the third level of computational resources to determine the identity of the human includes sending an identification query to an electronic device associated with the known user. In this example or any other example, the method further comprises sending a location query to an electronic device associated with the known user. In this example or any other example, one to all of the first, second, and third levels of computational resources of the smart assistant computer are dynamically scaled based on one or more security factors. In this example or any other example, a current level of computational resources dedicated to identifying the human is scaled up when the smart assistant computer is in a high security mode. In this example or any other example, a current level of computational resources dedicated to identifying the human is scaled up during a predetermined period. In this example or any other example, a current level of computational resources dedicated to identifying the human is scaled up when an unaccompanied protected user is present. In this example or any other example, computer-analyzing the data to recognize presence of the human includes detecting motion in the physical environment. In this example or any other example, motion detection begins after receiving an indication that an entrance door in the physical environment has opened. In this example or any other example, computer-analyzing the data to recognize presence of the human includes detecting presence of a known portable computing device in the physical environment.

In an example, a smart assistant computer comprises: a logic processor; and a storage device holding instructions executable by the logic processor to: receive data from one or more sensors configured to monitor a physical environment; computer-analyze the data to recognize presence of a human in the physical environment; and upon confirming an identity of the human, dedicate a first level of computational resources of the smart assistant computer to track the human; or upon failing to confirm the identity of the human while a known user is present, dedicate a second level of computational resources of the smart assistant computer, greater than the first level of computational resources, to determine the identity of the human; or upon failing to confirm the identity of the human while the known user is absent, dedicate a third level of computational resources of the smart assistant computer, greater than the second level of computational resources, to determine the identity of the human.

In an example, a method for a smart assistant computer to track a human comprises: receiving data from one or more sensors configured to monitor a physical environment; computer-analyzing the data to recognize presence of a human in the physical environment; if presence of the human is recognized in the environment, computer-analyzing the data to identify the human; if the human is identified, dedicating a first level of computational resources of the smart assistant computer to track the human; if the human is not identified, determining if a known user is present in the physical environment; if the known user is present in the physical environment, dedicating a second level of computational resources of the smart assistant computer greater than the first level of computational resources to track the human; and if the known user is not present in the physical environment, dedicating a third level of computational resources of the smart assistant computer greater than the second level of computational resources to track the human.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A method for a smart assistant computer to track a human, the method comprising:
   receiving data from one or more sensors configured to monitor a physical environment;
   computer-analyzing the data to recognize presence of a human in the physical environment and to determine the human to be one of the following: a previously identified human, an unidentified human in the presence of a known user, and an unidentified human not in the presence of a known user;
      based at least on determining the human to be a previously identified human, dedicating a first level of computational resources of the smart assistant computer to track the human;
      based at least on determining the human to be an unidentified human in the presence of a known user, dedicating a second level of computational resources of the smart assistant computer, greater than the first level of computational resources, to determine an identity of the human; and
      based at least on determining the human to be an unidentified human not in the presence of a known user, dedicating a third level of computational resources of the smart assistant computer, greater than the second level of computational resources, to determine the identity of the human.

2. The method of claim 1, where dedicating the first level of computational resources to track the human includes operating at least one of the one or more sensors at a reduced sampling frequency.

3. The method of claim 1, where dedicating the second level of computational resources to track the human includes operating at least one of the one or more sensors at an increased sampling frequency.

4. The method of claim 1, where dedicating the second level of computational resources to determine the identity of the human includes applying a first set of image processing algorithms to one or both of a visible-light image of the human captured by a visible-light camera of the one or more sensors or an infrared image of the human captured by an infrared camera of the one or more sensors.

5. The method of claim 4, where the first set of image processing algorithms includes one or more contrast adjustment algorithms.

6. The method of claim 5, where a contrast adjustment algorithm of the one or more contrast adjustment algorithms includes identifying lowest and highest pixel luminance values $L_i$ and $H_i$ in an infrared image of the physical environment, such values ranging from 0 to 255, and changing $L_i$ and $L_i$ to contrast-adjusted values $L_{CA}$ and $H_{CA}$, where $L_{CA}$ is given by $$\text{MAX}\left(30, \frac{Li}{2}\right),$$

and $H_{CA}$ is given by $$\text{MIN}\left(220, Hi + \frac{(255 - Hi)}{2}\right).$$

7. The method of claim 4, where dedicating the third level of computational resources to determine the identity of the human includes applying a second set of image processing algorithms to the visible-light image of the human, the second set of image processing algorithms requiring more processor operations than the first set of image processing algorithms.

8. The method of claim 1, where dedicating the third level of computational resources to determine the identity of the human includes prioritizing processor threads associated with human identification over processor threads associated with other tasks.

9. The method of claim 1, where dedicating the third level of computational resources to determine the identity of the human includes dedicating one or more user interface resources of the smart assistant computer to satisfy a security check.

10. The method of claim 1, where dedicating the third level of computational resources to determine the identity of the human includes sending an identification query to an electronic device associated with the known user.

11. The method of claim 10, where dedicating the third level of computational resources further comprises sending a location query to an electronic device associated with the known user.

12. The method of claim 1, where one to all of the first, second, and third levels of computational resources of the smart assistant computer are dynamically scaled based on one or more security factors.

13. The method of claim 12, where a current level of computational resources dedicated to identifying the human is scaled up when the smart assistant computer is in a high security mode.

14. The method of claim 12, where a current level of computational resources dedicated to identifying the human is scaled up during a predetermined period.

15. The method of claim 12, where a current level of computational resources dedicated to identifying the human is scaled up when an unaccompanied protected user is present.

16. The method of claim 1, where computer-analyzing the data to recognize presence of the human includes detecting motion in the physical environment.

17. The method of claim 16, where motion detection begins after receiving an indication that an entrance door in the physical environment has opened.

18. The method of claim 1, where computer-analyzing the data to recognize presence of the human includes detecting presence of a known portable computing device in the physical environment.

19. A smart assistant computer, comprising:
a logic processor; and
a storage device holding instructions executable by the logic processor to:
receive data from one or more sensors configured to monitor a physical environment;
computer-analyze the data to recognize presence of a human in the physical environment and to determine the human to be one of the following: a previously identified human, an unidentified human in the presence of a known user, and an unidentified human not in the presence of a known user;
based at least on determining the human to be a previously identified human, dedicate a first level of computational resources of the smart assistant computer to track the human;
based at least on determining the human to be an unidentified human in the presence of a known user, dedicate a second level of computational resources of the smart assistant computer, greater than the first level of computational resources, to determine an identity of the human; and
based at least on determining the human to be an unidentified human not in the presence of a known user, dedicate a third level of computational resources of the smart assistant computer, greater than the second level of computational resources, to determine the identity of the human.

20. A method for a smart assistant computer to track a human, the method comprising:
receiving data from one or more sensors configured to monitor a physical environment;
computer-analyzing the data to recognize presence of a human in the physical environment;
if presence of the human is recognized in the environment, computer-analyzing the data to identify the human;
if the human is identified, dedicating a first level of computational resources of the smart assistant computer to track the human;
if the human is not identified, determining if a known user is present in the physical environment;
if the known user is present in the physical environment, dedicating a second level of computational resources of the smart assistant computer greater than the first level of computational resources to track the human; and
if the known user is not present in the physical environment, dedicating a third level of computational resources of the smart assistant computer greater than the second level of computational resources to track the human.

* * * * *